US007857814B2

(12) United States Patent
Haines

(10) Patent No.: US 7,857,814 B2
(45) Date of Patent: Dec. 28, 2010

(54) METHODS AND APPARATUS FOR MINIMALLY INVASIVE ARTHROPLASTY

(75) Inventor: Timothy G. Haines, Seattle, WA (US)

(73) Assignee: Hudson Surgical Design, Inc., Seattle, WA (US)

( * ) Notice: Subject to any disclaimer, the term of this patent is extended or adjusted under 35 U.S.C. 154(b) by 1265 days.

(21) Appl. No.: 11/075,828

(22) Filed: Mar. 8, 2005

(65) Prior Publication Data
US 2006/0015117 A1 Jan. 19, 2006

Related U.S. Application Data

(63) Continuation-in-part of application No. 11/049,634, filed on Feb. 2, 2005, now abandoned, and a continuation-in-part of application No. 11/036,584, filed on Jan. 14, 2005.

(60) Provisional application No. 60/551,078, filed on Mar. 8, 2004, provisional application No. 60/551,080, filed on Mar. 8, 2004, provisional application No. 60/551,096, filed on Mar. 8, 2004, provisional application No. 60/551,631, filed on Mar. 8, 2004, provisional application No. 60/551,307, filed on Mar. 8, 2004, provisional application No. 60/551,262, filed on Mar. 8, 2004, provisional application No. 60/551,160, filed on Mar. 8, 2004, provisional application No. 60/536,320, filed on Jan. 14, 2004, provisional application No. 60/540,992, filed on Feb. 2, 2004.

(51) Int. Cl.
*A61F 5/00* (2006.01)
(52) U.S. Cl. .................................. 606/86 R
(58) Field of Classification Search .......... 606/79–82, 606/86–88; 623/20.14
See application file for complete search history.

(56) References Cited

U.S. PATENT DOCUMENTS 3,739,662 A 6/1973 Windelman et al.

(Continued)

FOREIGN PATENT DOCUMENTS

EP 0189253 7/1986

(Continued)

OTHER PUBLICATIONS

T.D.V. Cooke et al., *Universal Bone Cutting Device for Precision Knee Replacement Arthroplasty and Osteotomy*, 7 J. Biomed. Eng'g 45, 47, col. 2, ll. 52-57 (1985).

(Continued)

*Primary Examiner*—Thomas C Barrett
*Assistant Examiner*—Michael J Araj
(74) *Attorney, Agent, or Firm*—Patterson, Thuente, Skaar & Christensen, P.A.

(57) ABSTRACT

A cutting tool for creating resected surfaces of bone during arthroplasty procedures has a single offset handle arm that presents a narrower effective width than a width of the cutting profile of the cutting tool along a longitudinal axis of the cutting profile. Preferably, the single offset handle arm creates a cutting tool with a generally L-shaped outline simultaneously accounting for soft tissue/incision geometry and bony geometry to accommodate both in facilitating ease of use and minimal displacement of soft tissue during cutting. The cutting tool can be snaked into position through an incision approximately the size of the width of the handle arm, instead of requiring an incision that is essentially the width of the cutting path of the cutting tool. In alternate embodiments, the cutting tool is a milling tool, a wireplasty cutting tool, a band saw or reciprocating cutting tool.

10 Claims, 22 Drawing Sheets

U.S. PATENT DOCUMENTS

| | | |
|---|---|---|
| 3,774,244 A | 11/1973 | Walker |
| 3,798,679 A | 3/1974 | Ewald |
| 3,816,855 A | 6/1974 | Salch |
| 3,906,550 A | 9/1975 | Rostoker |
| 3,953,899 A | 5/1976 | Charnley |
| 4,069,824 A | 1/1978 | Weinstock |
| 4,178,641 A | 12/1979 | Gruendel |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Peterson |
| 4,568,348 A | 2/1986 | Johnson et al. |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,709,699 A | 12/1987 | Michael |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,822,365 A | 4/1989 | Walker |
| 4,841,975 A | 6/1989 | Woolson |
| 4,880,429 A | 11/1989 | Stone |
| 4,892,093 A | 1/1990 | Zarnowski |
| 4,896,663 A | 1/1990 | Vandewalle |
| 4,919,667 A | 4/1990 | Richmond |
| 4,938,762 A | 7/1990 | Wehrli |
| 4,952,213 A | 8/1990 | Bowman |
| 4,971,075 A | 11/1990 | Lee |
| 5,002,545 A | 3/1991 | Whiteside |
| 5,002,547 A | 3/1991 | Poggie |
| 5,007,934 A | 4/1991 | Stone |
| 5,021,056 A | 6/1991 | Hofman |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,092,869 A | 3/1992 | Waldron |
| 5,098,436 A | 3/1992 | Ferrante |
| 5,100,409 A | 3/1992 | Coates |
| 5,112,336 A | 5/1992 | Krevolin |
| 5,122,144 A | 6/1992 | Bert |
| 5,129,909 A | 7/1992 | Sutherland |
| 5,147,365 A | 9/1992 | Whitlock |
| 5,176,710 A | 1/1993 | Hahn |
| 5,190,547 A | 3/1993 | Barber, Jr. |
| 5,206,023 A | 4/1993 | Hunziker |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,875 A | 8/1993 | Trigg |
| 5,250,050 A | 10/1993 | Poggie |
| 5,263,498 A | 11/1993 | Caspari |
| 5,269,786 A | 12/1993 | Morgan |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,342,368 A | 8/1994 | Peterson |
| 5,358,527 A | 10/1994 | Forte |
| 5,358,529 A | 10/1994 | Davidson |
| 5,364,401 A | 11/1994 | Ferreante |
| 5,364,402 A | 11/1994 | Mumme |
| 5,370,699 A | 12/1994 | Hood |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,514,136 A | 5/1996 | Richelsoph |
| 5,514,139 A | 5/1996 | Goldstein |
| 5,514,143 A | 5/1996 | Bonutti |
| 5,520,695 A | 5/1996 | Luckman |
| 5,540,695 A | 7/1996 | Levy |
| 5,542,947 A | 8/1996 | Treacy |
| 5,571,100 A | 11/1996 | Goble |
| 5,578,039 A | 11/1996 | Vendrely |
| 5,593,411 A | 1/1997 | Stalcup |
| 5,597,379 A | 1/1997 | Haines |
| 5,601,563 A | 2/1997 | Burke |
| 5,611,802 A | 3/1997 | Samuelson |
| 5,628,749 A | 5/1997 | Vendrely |
| 5,643,272 A | 7/1997 | Haines |
| 5,649,928 A | 7/1997 | Grundei |
| 5,653,714 A * | 8/1997 | Dietz et al. .................. 606/87 |
| 5,658,293 A | 8/1997 | Vanlaningham |
| 5,667,511 A | 9/1997 | Vendrely |
| 5,682,886 A | 11/1997 | Delp |
| 5,690,635 A | 11/1997 | Matsen, III |
| 5,690,637 A | 11/1997 | Wen |
| 5,697,935 A | 12/1997 | Moran |
| 5,723,016 A | 3/1998 | Minns et al. |
| 5,725,530 A | 3/1998 | Popken |
| 5,755,803 A | 5/1998 | Haines |
| 5,769,855 A | 6/1998 | Bertin |
| 5,769,899 A | 6/1998 | Schwartz |
| 5,799,055 A | 8/1998 | Peshkin |
| 5,810,827 A | 9/1998 | Haines |
| 5,824,105 A | 10/1998 | Ries |
| 5,871,546 A | 2/1999 | Colleran |
| 5,879,354 A | 3/1999 | Haines |
| 5,906,643 A | 5/1999 | Walker |
| 5,980,526 A | 11/1999 | Johnson |
| 5,986,169 A | 11/1999 | Gjunter |
| 6,039,764 A | 3/2000 | Pottenger |
| 6,056,754 A | 5/2000 | Haines |
| 6,059,788 A | 5/2000 | Katz |
| 6,132,468 A | 10/2000 | Mansmann |
| 6,171,340 B1 | 1/2001 | McDowell |
| 6,197,064 B1 | 3/2001 | Haines |
| 6,236,875 B1 | 5/2001 | Becholz |
| 6,285,902 B1 | 9/2001 | Kienzle |
| 6,340,363 B1 | 1/2002 | Bolger |
| 6,342,075 B1 | 1/2002 | MacArthur |
| 6,348,058 B1 | 2/2002 | Melkent |
| 6,368,353 B1 | 4/2002 | Arcand |
| 6,375,658 B1 | 4/2002 | Hangody |
| 6,401,346 B1 | 6/2002 | Roberts |
| 6,430,434 B1 | 8/2002 | Mittelstadt |
| 6,458,128 B1 | 10/2002 | Schulze |
| 6,470,207 B1 | 10/2002 | Simon |
| 6,477,400 B1 | 11/2002 | Barrick |
| 6,482,409 B1 | 11/2002 | Lobb |

| | | |
|---|---|---|
| 6,491,699 B1 | 12/2002 | Henderson |
| 6,520,964 B2 | 2/2003 | Tallarida |
| 6,554,838 B2 | 4/2003 | McGovern |
| 6,575,980 B1 | 6/2003 | Robie |
| 6,579,290 B1 | 6/2003 | Hardcastle |
| 6,595,997 B2 | 7/2003 | Axelson, Jr. et al. |
| 6,679,917 B2 | 1/2004 | Ek |
| 6,685,711 B2 | 2/2004 | Axelson |
| 6,694,168 B2 | 2/2004 | Traxel |
| 6,694,768 B2 | 2/2004 | Lu |
| 6,695,848 B2 | 2/2004 | Haines |
| 6,697,664 B2 | 2/2004 | Kienzle |
| 6,701,174 B1 | 3/2004 | Krause |
| 6,702,821 B2 * | 3/2004 | Bonutti ................. 606/88 |
| 6,711,432 B1 | 3/2004 | Krause et al. |
| 6,725,080 B2 | 4/2004 | Melkent et al. |
| 6,755,563 B2 | 6/2004 | Wahlig et al. |
| 6,672,224 B2 | 7/2004 | Tallarida |
| 6,783,550 B2 | 8/2004 | MacArthur |
| 6,796,988 B2 | 9/2004 | Melkent et al. |
| 6,827,723 B2 | 12/2004 | Carson |
| 6,858,032 B2 * | 2/2005 | Chow et al. ................. 606/80 |
| 6,875,222 B2 | 4/2005 | Long |
| 6,898,858 B1 | 5/2005 | Spell |
| 6,916,324 B2 | 7/2005 | Sanford |
| 6,942,627 B2 | 9/2005 | Huitema |
| 6,942,694 B2 | 9/2005 | Liddicoat |
| 7,018,418 B2 | 3/2006 | Amrich |
| 7,029,477 B2 | 4/2006 | Grimm |
| 7,048,741 B2 | 5/2006 | Swanson |
| 7,077,867 B1 | 7/2006 | Pope |
| 7,104,966 B2 * | 9/2006 | Shiber ................. 600/585 |
| 7,104,996 B2 | 9/2006 | Bonutti |
| 7,141,053 B2 | 11/2006 | Rosa |
| 7,172,596 B2 | 2/2007 | Coon |
| 7,175,630 B2 | 2/2007 | Farling |
| 7,241,298 B2 | 7/2007 | Nemec |
| 7,326,252 B2 | 2/2008 | Otto |
| 7,344,541 B2 | 3/2008 | Haines |
| 7,371,240 B2 | 5/2008 | Pinczewski |
| 7,422,605 B2 | 9/2008 | Burstein |
| 7,491,235 B2 | 2/2009 | Fell |
| 2001/0044627 A1 | 11/2001 | Justin |
| 2003/0069585 A1 | 4/2003 | Axelson |
| 2003/0069591 A1 | 4/2003 | Carson |
| 2003/0181986 A1 | 9/2003 | Buchholz |
| 2003/0212413 A1 | 11/2003 | Wilk |
| 2004/0039396 A1 | 2/2004 | Couture |
| 2004/0122305 A1 | 6/2004 | Grimm |
| 2004/0152970 A1 | 8/2004 | Hunter |
| 2004/0153066 A1 | 8/2004 | Coon |
| 2004/0249471 A1 | 12/2004 | Bindseil |
| 2005/0149038 A1 | 7/2005 | Haines |
| 2005/0149039 A1 | 7/2005 | Haines |
| 2005/0149040 A1 | 7/2005 | Haines |
| 2005/0171604 A1 | 8/2005 | Michalow |
| 2006/0015109 A1 | 1/2006 | Haines |
| 2006/0015115 A1 | 1/2006 | Haines |
| 2006/0015116 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero |
| 2006/0058882 A1 | 3/2006 | Haines |
| 2007/0078517 A1 | 4/2007 | Engh |
| 2007/0179607 A1 | 8/2007 | Hodorek |
| 2008/0154270 A1 | 6/2008 | Haines |
| 2009/0076514 A1 | 3/2009 | Haines |
| 2009/0082773 A1 | 3/2009 | Haines |
| 2009/0138018 A1 | 5/2009 | Haines |

FOREIGN PATENT DOCUMENTS

| | | |
|---|---|---|
| EP | 0466659 A2 | 1/1992 |
| EP | 0538153 A1 | 4/1993 |
| EP | 0682916 A2 | 11/1995 |
| EP | 0761242 | 3/1997 |
| FR | 2664157 A1 | 1/1992 |
| GB | 2007980 | 7/1982 |
| JP | 2002/274214 | 11/1990 |
| SU | 577020 T | 10/1977 |
| WO | WO96/01588 | 1/1996 |
| WO | WO96/07361 A1 | 3/1996 |
| WO | WO 97/05827 | 2/1997 |
| WO | WO97/29703 A1 | 8/1997 |
| WO | WO97/29704 A1 | 8/1997 |
| WO | WO02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

E. Marlowe Goble and Daniel F. Justin, *Minimally invasive total knee replacement: principles and technique*, Orthop. Clin. N. Am. 35 (2004) 235-245.
Whiteside Ortholoc Total Knee System: Surgical Procedure, Dow Corning Wright, pp. WMT000001-WMT000040, Jun. 1985.
Zimmer, Insall/Burstein II, *Constrained Condylar: Modular Knee System*, 35 pages, copyright 1989.
File History for U.S. Appl. No. 12/187,210, filed Aug. 6, 2008.
File History for U.S. Appl. No. 11/075,842, filed Mar. 8, 2005.
File History for U.S. Appl. No. 11/075,836, filed Mar. 8, 2005.
U.S. Appl. No. 12/171,843, Inventor: Haines, filed Jul. 11, 2008.
U.S. Appl. No. 11/036,584, Inventor: Timothy Haines, filed Jan. 14, 2005.
File History for U.S. Appl. No. 11/075,840, filed Mar. 8, 2005.
U.S. Appl. No. 11/075,552, Inventor: Haines, filed Mar. 8, 2005.
U.S. Appl. No. 11/825,857, Inventor: Haines, filed Jul. 9, 2007.
File History for U.S. Appl. No. 11/049,634, filed Feb. 5, 2005.
File History for U.S. Appl. No. 11/074,599, filed Mar. 8, 2005.
File History for U.S. Appl. No. 11/075,553, filed Mar. 8, 2005.
Whiteside Ortholoc Total Knee System, Dow Corning Wright, pp. ZH000109679-ZH000109690.
Zimmer, Insall/Burstein II, *Modular Knee System*, Surgical Technique, pp. ZH000109691-ZH000109710.
Zimmer, The Miller/Galante Advantage: Total Knee System, pp. ZH000156953-ZH000156968.

* cited by examiner

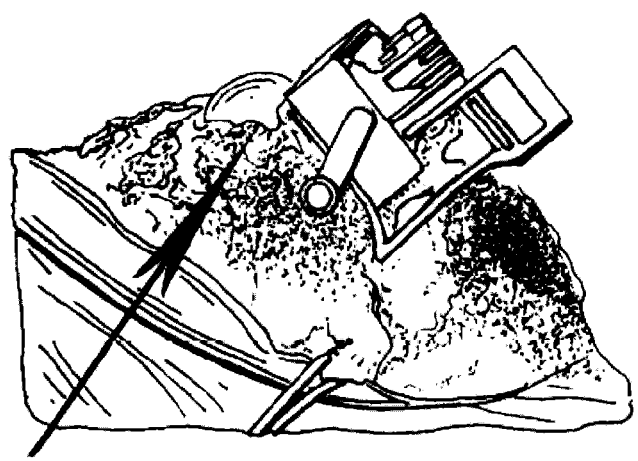
FEMUR    *Fig.3A*
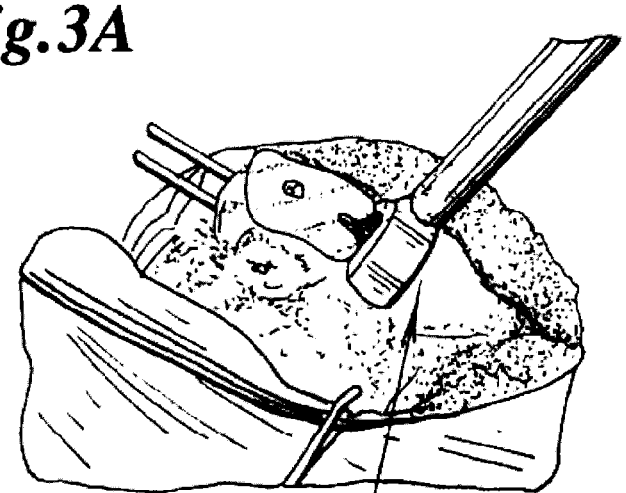
*Fig.3B*    TIBIA
PATELLA
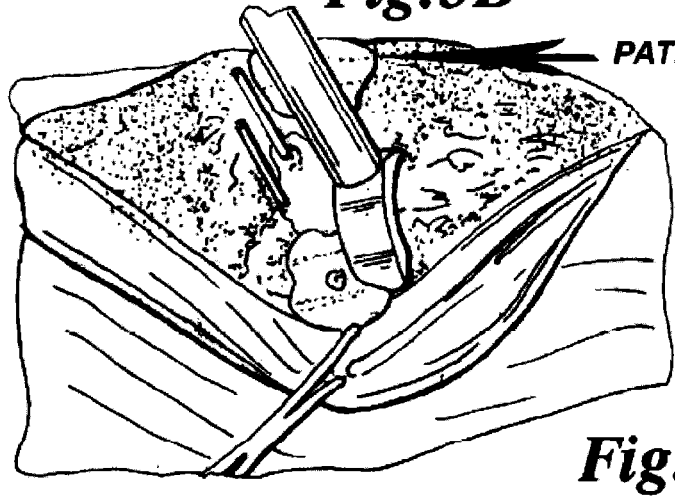
*Fig.3C*

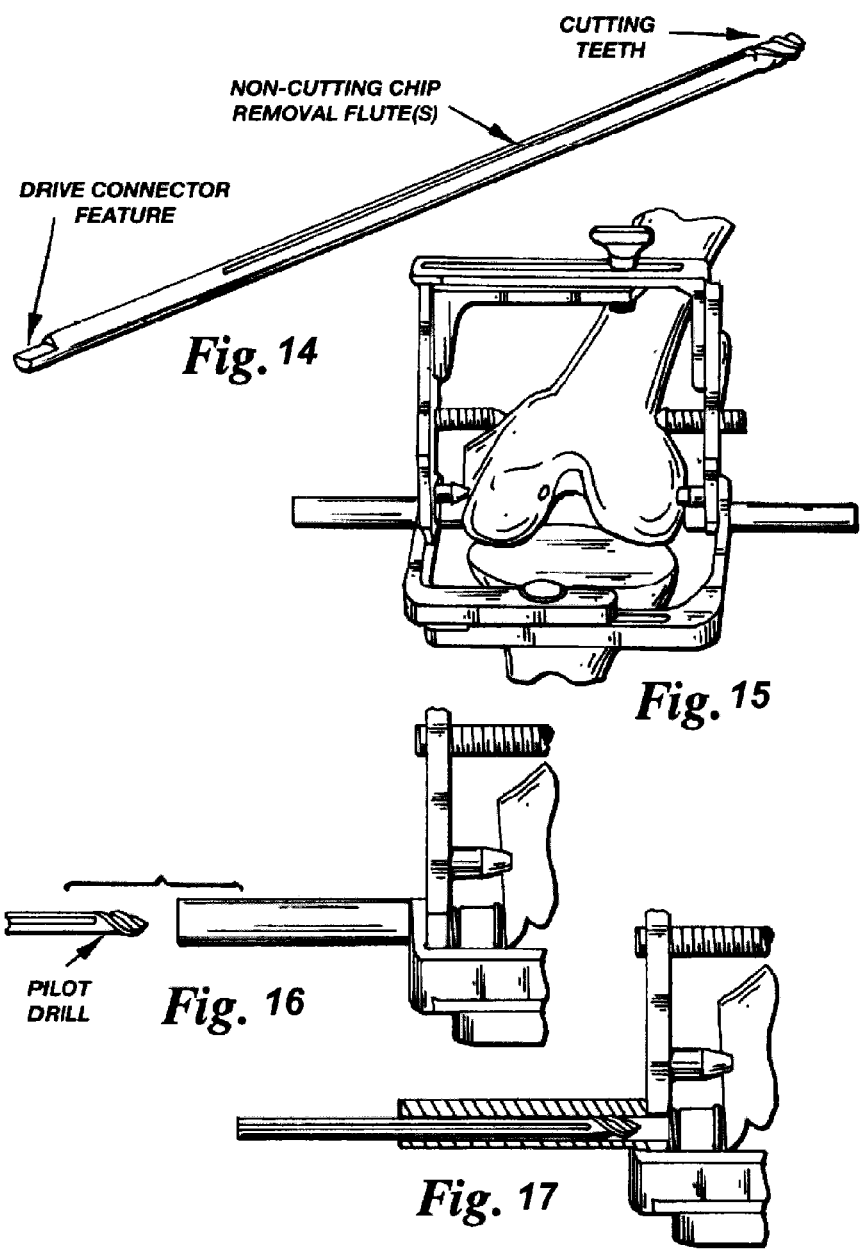

SIDE CUTTING DRILL

BONE REMNANTS TO BE REMOVED

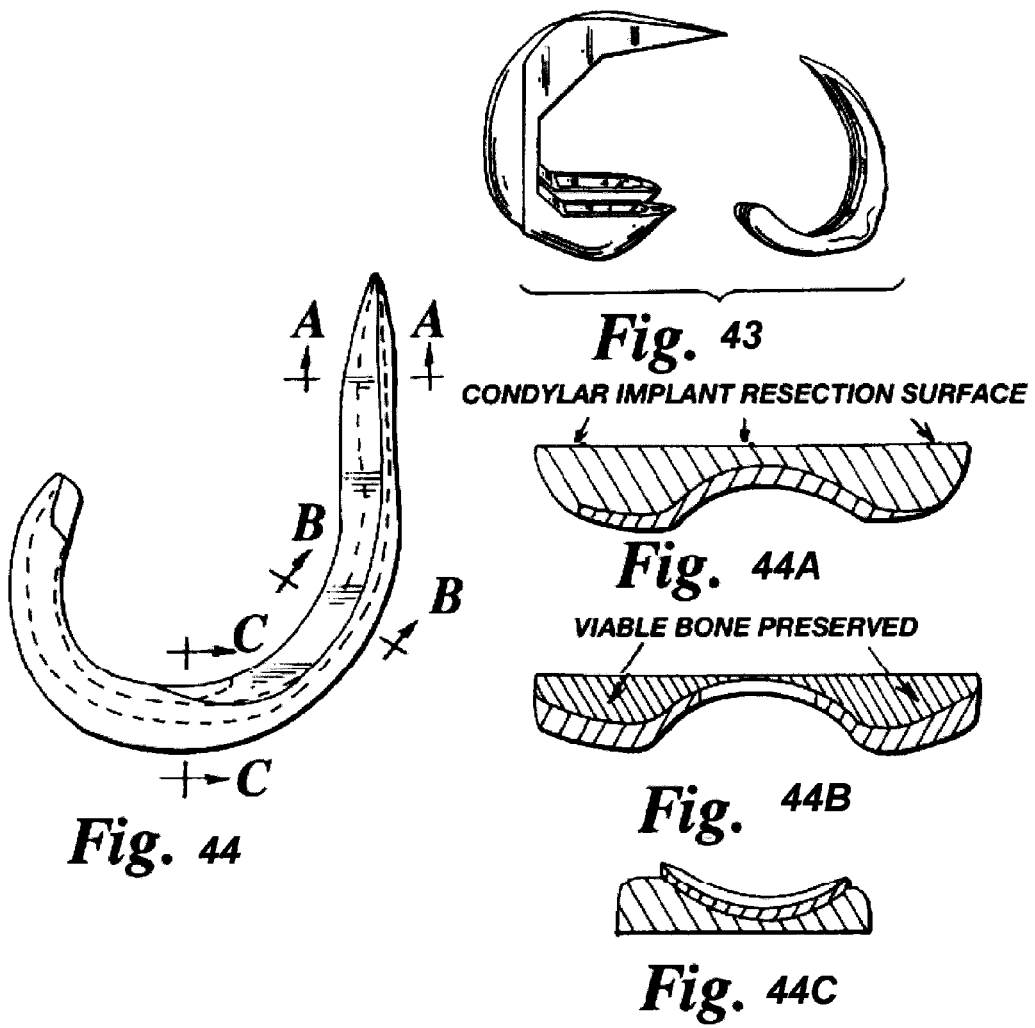

LINKING BRIDGE

ALTERNATE OFFSET RAIL LOCATION

METHODS AND APPARATUS FOR MINIMALLY INVASIVE ARTHROPLASTY

CLAIM TO PRIORITY

The present invention claims priority to U.S. Provisional Application No. 60/551,078, filed Mar. 8, 2004, entitled, "METHODS AND APPARATUS FOR MINIMALLY INVASIVE RESECTION," and claims priority to U.S. Provisional Application No. 60/551,080, filed Mar. 8, 2004, entitled, "METHODS AND APPARATUS FOR PIVOTABLE GUIDE SURFACES FOR ARTHROPLASTY," and claims priority to U.S. Provisional Application No. 60/551,096, filed Mar. 8, 2004, entitled, "METHODS AND APPARATUS FOR ENHANCED RETENTION OF PROSTHETIC IMPLANTS," and claims priority to U.S. Provisional Application No. 60/551,631, filed Mar. 8, 2004, entitled, "METHODS AND APPARATUS FOR CONFORMABLE PROSTHETIC IMPLANTS," and claims priority to U.S. Provisional Application No. 60/551,307, filed Mar. 8, 2004, entitled, "METHODS AND APPARATUS FOR IMPROVED CUTTING TOOLS FOR RESECTION," and claims priority to U.S. Provisional Application No. 60/551,262, filed Mar. 8, 2004, entitled, "METHODS AND APPARATUS FOR IMPROVED DRILLING AND MILLING TOOLS FOR RESECTION," and claims priority to U.S. Provisional Application No. 60/551,160, filed Mar. 8, 2004, entitled, "METHODS AND APPARATUS FOR IMPROVED PROFILE BASED RESECTION," and is a continuation-in-part of U.S. patent application Ser. No. 11/036,584, filed Jan. 14, 2005, entitled, "METHODS AND APPARATUS FOR PINPLASTY BONE RESECTION," which claims priority to U.S. Provisional Application No. 60/536,320, filed Jan. 14, 2004, and is a continuation-in-part of U.S. patent application Ser. No. 11/049,634, filed Feb. 2, 2005, now abandoned entitled, "METHODS AND APPARATUS FOR WIREPLASTY BONE RESECTION," which claims priority to U.S. Provisional Application No. 60/540,992, filed Feb. 2, 2004, entitled, "METHODS AND APPARATUS FOR WIREPLASTY BONE RESECTION," the entire disclosures of which are hereby fully incorporated by reference.

BACKGROUND OF THE INVENTION

1. Field of the Invention

This invention generally relates to methods and apparatus for bone resection to allow for the interconnection or attachment of various prosthetic devices with respect to the patient. More particularly, the present invention relates to methods and apparatus for minimally invasive arthroplasty that permits bone resection at a joint through smaller incisions and with less potential for soft tissue damage.

2. Background Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint.

Even though the trend in many surgical procedures has been to adopt techniques that are minimally invasive so as to reduce both the size of the incision and the amount of damage to soft tissue surrounding the joint, the need for precision in the location and orientation of resected bone cuts for arthroplasty procedures has limited the use of existing minimally invasive surgical techniques. Conventionally, femoral and tibial resections in total knee arthroplasty have been performed primarily through an incision made across the anterior (front) of the knee joint. U.S. Pat. No. 5,810,827 shows a technique for arthroplasty that involves making the resection cuts via incisions on either the medial or lateral sides. A similar approach to minimally invasive techniques for knee arthroplasty is described in U.S. Patent Publ. Appls. 2003/0100906A1, 2003/0171757A1 and 2003/0212413A1. While a medial or lateral approach has the potential to reduce soft tissue damage as compared to the anterior approach of conventional arthroplasty techniques, the size of the incision is still dictated by the size of the cutting tools and the size of the prosthetic implants.

Efforts have been made to reduce the effective size of prosthetic implants, either by making the prosthetic implant smaller or by making the prosthetic implant modular. The unicondular or "uni" implant for knee replacements, for example, is designed to replace just one of the two condyles on the femur and therefore is smaller than the implant prosthesis required for a total knee arthroplasty (TKA). Modular implants, where the implant is comprised of multiple interlocking components, have been used for both knee and hip replacements as another approach to making the size of the prosthetic implant smaller.

Although the effective size of prosthetic implants is being made smaller, it would be desirable to provide instrumentation and cutting tools that also reduced the requirements for incision size and minimized soft tissue damage, while still being able to provide the necessary precision and location to create the resected surfaces for such implants.

SUMMARY OF THE INVENTION

The present invention provides for embodiments of cutting guides, cutting tools, and soft tissue management techniques that permit the use of cutting tools with a single offset handle arm that presents a narrower effective width than the width of the cutting path of the cutting tool along the longitudinal axis of the cutting tool. The width of the handle arm is measured in the same plane as the plane of the cutting profile of the cutting tool. Preferably, the single offset handle arm creates a cutting tool with a generally L-shaped outline simultaneously accounting for soft tissue/incision geometry and bony geometry to accommodate both in facilitating ease of use and minimal displacement of soft tissue during cutting. The cutting tool in accordance with the present invention can be snaked into position through an incision approximately the size of the width of the handle arm, instead of requiring an incision that is essentially the width of the cutting path of the cutting tool. In one embodiment, the cutting tool is a milling tool. In alternate embodiments, the cutting tool is a wireplasty cutting tool or a band saw or reciprocating cutting tool.

Another preferred embodiment of the present invention is Transcutaneous Transarticular Arthroplasty wherein the cutting tools extend through minimalist soft tissue portal(s) or stab wound(s) and across, through, beneath, or about the articular surface to be repaired. This embodiment in knee arthroplasty takes advantage of the fact that the soft tissues surrounding the joint line of the knee, especially the capsule, ligaments and tendons, move in concert with movement of the tibia about the femur. Thus the cutting path of the cutting tool with respect to the femur is geometrically similar to the kinematic path of the capsule, ligaments, skin and tendons of the joint as the tibia is manipulated through a range of motion about the femur and thereby the kinematic path of a portal through these soft tissues is similar enough to allow for completion of some or all cuts through a soft tissue portal little larger than the diameter, size or cross-section of the cutting tool.

The present invention is preferably utilized with a number of embodiments of cutting guide technologies loosely or directly based on Profile Based Resection (PBR). The present invention can be used with external guide surfaces, although internal guide surfaces or a hybrid of internal and external guide surfaces may also be utilized. The overriding objects of PBR technologies are to provide for significantly improved reproducibility of implant fit and alignment in a manner largely independent of the individual surgeon's manual skills, while providing for outstanding ease of use, economic, safety, and work flow performance.

The present invention may utilize any number of embodiments of alignment or drill guides to precisely and accurately determine the desired cutting guide location/orientation, thus cut surface location(s)/orientation(s), thus prosthetic implant location and orientation. The overriding objects of the embodiments are to precisely and accurately dictate the aforementioned locations and orientations while optionally enabling ease of use in conjunction with manually or Computer Assisted techniques, and while optionally enabling ease of use in minimally invasive procedures where surgical exposure and trauma are minimized.

The present invention utilizes a number of embodiments of cutting tools to remove bony material to create cut surfaces for prosthetic implant attachment and fixation. The overriding objects of the embodiments are to provide the ability to perform resection in very small incisions, the creation of precise and accurate cut(s), and to provide for soft tissue protection characteristics and features preventing the tool from accidentally harming soft tissue. Specifically, many of the cutting tool embodiments disclosed are either incapable or highly resistant to damaging soft tissue, or are by means disclosed prevented from coming into contact with soft tissue in the first place.

The present invention utilizes a number of methods and apparatus embodiments of soft tissue management techniques and the devices supporting said techniques. The overriding object of these embodiments is to take advantage of the anatomy, physiology, and kinematics of the human body in facilitating clinical efficacy of orthopedic procedures. Another way of stating this is that it is an object of these embodiments to seek those synergies that exist between the way the body works and the needs of surgical techniques to allow both the surgical process and the end result to be ideal, as opposed to conventional surgical intervention techniques which are antagonistic to the sought after goals of treatment thus requiring prolonged recovery and mitigation of clinical benefit.

It is an often repeated rule of thumb for orthopedic surgeons that a "Well placed, but poorly designed implant will perform well clinically, while a poorly placed, well designed implant will perform poorly clinically." The present invention provides a method and apparatus for reducing implant placement errors in order to create more reproducible, consistently excellent clinical results in a manner that decreases risk to soft tissue, incision or exposure size requirements, manual skill requirements, and/or visualization of cutting action.

It should be clear that applications of the present invention is not limited to Total Knee Arthroplasty or the other specific applications cited herein, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where minimal expense, accuracy, precision, soft tissue protection or preservation, minimal incision size or exposure are required or desired for a bone resection and/or prosthetic implantation is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

The patent or application file contains at least one drawing executed in color. Copies of this patent with color drawing(s) will be provided by the Patent and Trademark Office upon request and payment of the necessary fee.

Other important objects and features of the invention will be apparent from the following detailed description of the invention taken in connection with the accompanying drawings in which:

FIGS. 1, 2, and 3 are pictorial representations standard incision sizes or exposure required by the prior art, while

FIGS. 5-51 show various depictions of embodiments and methods in accordance with alternate embodiments of the present invention.

DETAILED DESCRIPTION OF THE PREFERRED EMBODIMENTS

It should be noted that, in many of the figures, the cut surface created by the cutting tool in accordance with the techniques of the present invention are shown as having already been completed for the sake of clarity. Similarly, the bones may be shown as being transparent or translucent for the sake of clarity. The guides/pins, cutting tool, bones, and other items disclosed are may be similarly represented for the sake of clarity or brevity FIGS. 1 through 4

Figure 1:
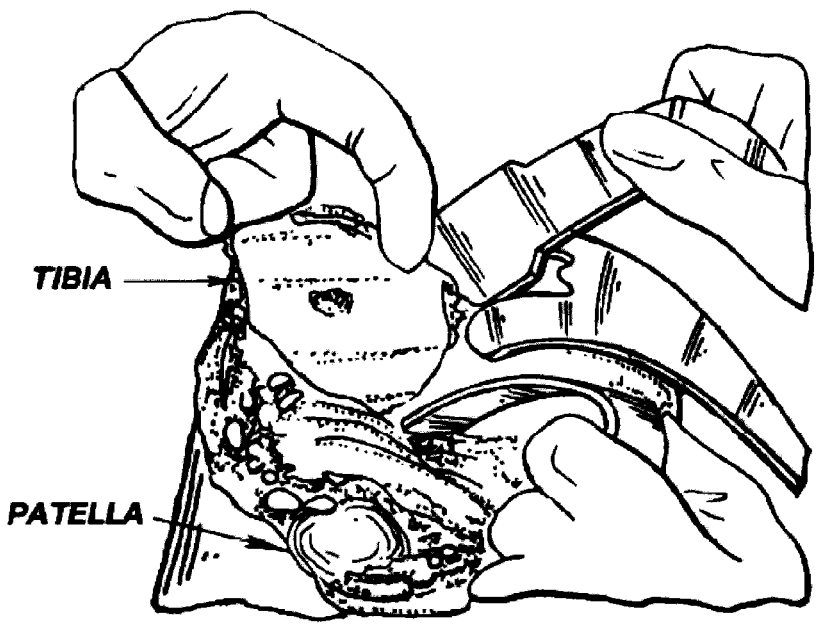
Figure 2:
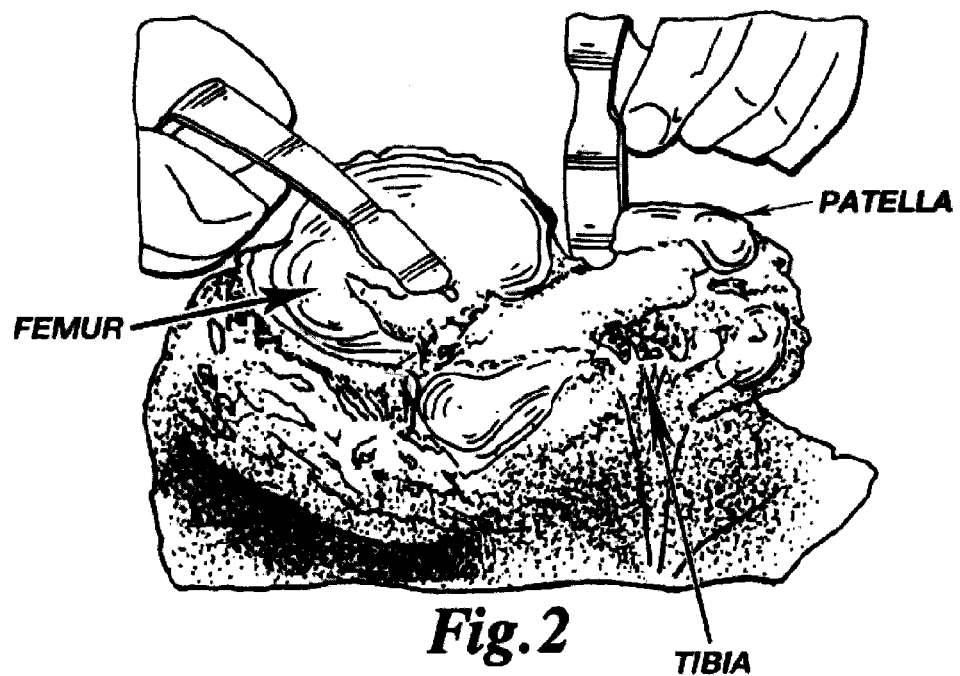
Figure 4:
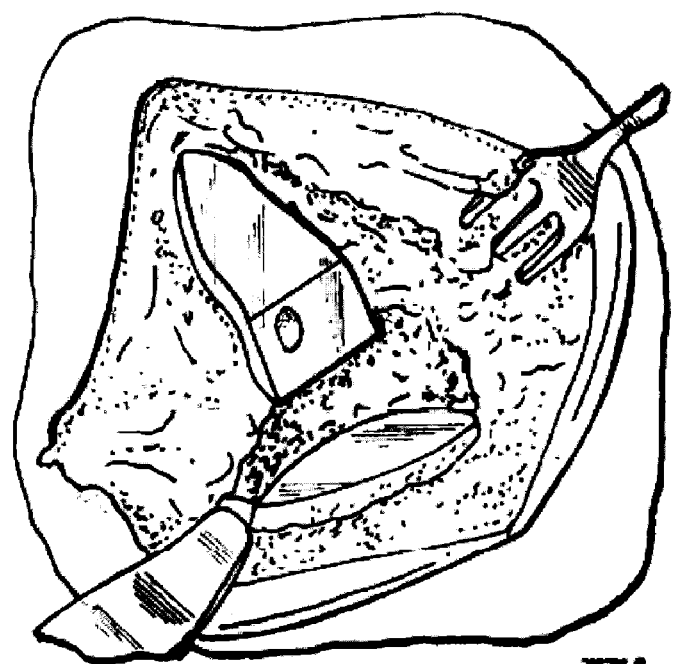
FIG. 4 is a pictorial representation or approximation of one form of surgical exposure that is desired.

FIGS. 1 and 2 show conventional surgical exposures and instrumentation being utilized. FIG. 4 shows a reduced incision currently utilized in performing the current state of the art in 'minimally invasive' Unicondylar Knee Replacement.

FIGS. 5 through 10

FIGS. 5 through 10 show embodiments of the present invention for femoral resection. For the sake of clarity, it should be noted that any combination of the forms of the present invention disclosed herein may be modified or combined to form constructs not specifically disclosed herein, but still within the scope of the present invention. One of ordinary skill in the art would clearly recognize the applicability and benefits of the present invention for tibial and/or femoral resection in Unicondylar or Bicondylar procedures, for bone resection in ankle replacement or arthrodesis (fusion), mandibular advancement procedures, high tibial osteotomy procedures, proximal femoral and acetabular preparation in Hip Arthroplasty, and a list of other applications where reproducible and safe removal of living tissue during surgical intervention is beneficial.

FIGS. 5-10 show embodiments of the present invention that include a milling cutting tool having a cutting path defined along a side of the longitudinal axis of the cutting tool. Another embodiment of a cutting tool for use in accordance with the present invention is described in co-pending U.S. patent application Ser. No. 11/049,634, filed Feb. 3, 2005, entitled, "METHODS AND APPARATUS FOR WIREPLASTY BONE RESECTION," which claims priority to U.S. provisional patent application Ser. No. 60/540,992, filed Feb. 2, 2004, entitled "METHOD AND APPARATUS FOR WIREPLASTY BONE RESECTION", the disclosures of which are incorporated by reference.

FIGS. 5-10 shows an embodiment of the present invention wherein the guide plates and guide surfaces are located entirely outside the wound, but the side cutting drill and handle construct are not passed through mediolateral soft tissue portals described hereinabove. The side cutting drill controlling portion of the handle is essentially 'snaked' into the less invasive wound/exposure/approach/incision and the guide engagement features are engaged to the cutting guide at a location entirely outside the wound. As long as the axis of the engagement feature is maintained as coaxial with the side cutting drill, the desired cut geometries will be attained despite manipulation of the handle with respect to the guide. This method can be utilized to complete some or all of the desired cuts. Also, this embodiment of the current invention can be used to perform the posterior cut, posterior chamfer cut, and distal cut optionally using kinematic resection to reduce exposure requirements, and then removed from the wound and guide, flipped over 180 degrees from the orientation shown in FIG. 9, reinserted into the wound and into engagement with the guide to cut the anterior chamfer cut and anterior cut with or without implementation of a kinematic resection technique and, optionally, with the knee in 15 degrees to 45 degrees to facilitate the soft tissue laxity and ease of use previously described. It should be noted that the mechanism for driving the side cutting drill is not represented in these figures and that a number of different options may be used. One way to accomplish drive input is generically represented in FIG. 10, where a flexible drive shaft or bevel gear arrangement may be utilized to drive the side cutting form drill shown. Alternatively, chain, belt, or pneumatic drive mechanisms may also be used.

Figure 10:
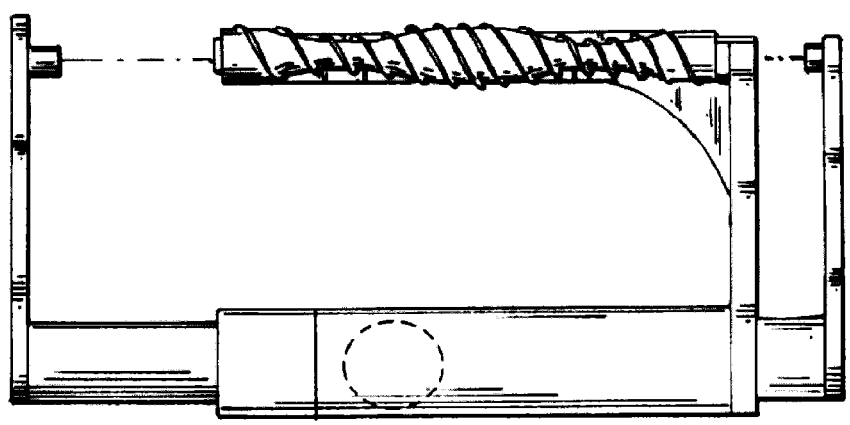
Figure 11:
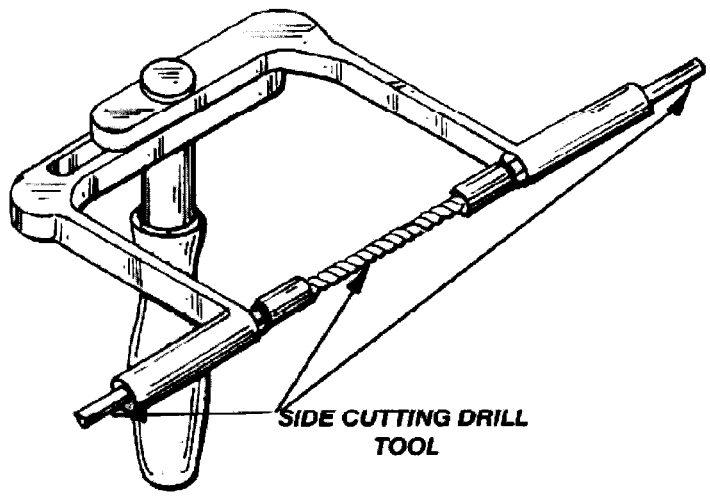
Figures 31A, 31B:
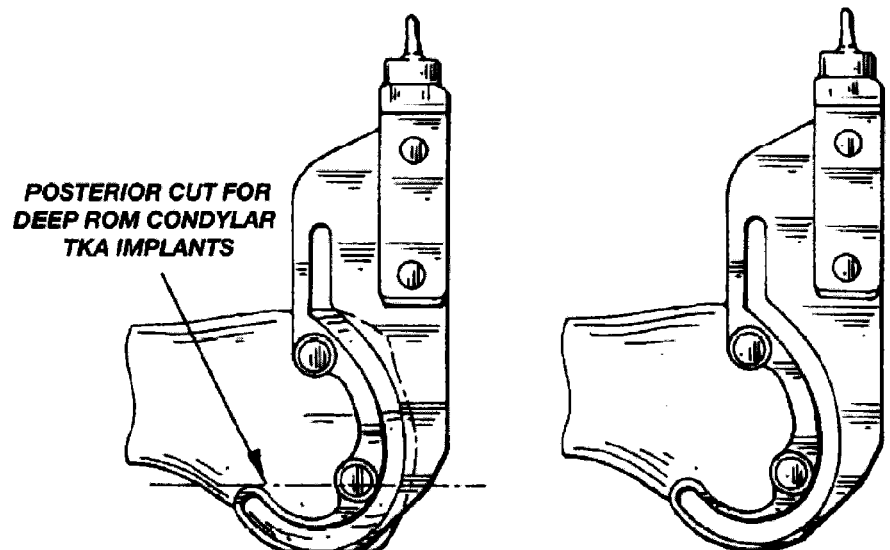
Figures 32, 33:
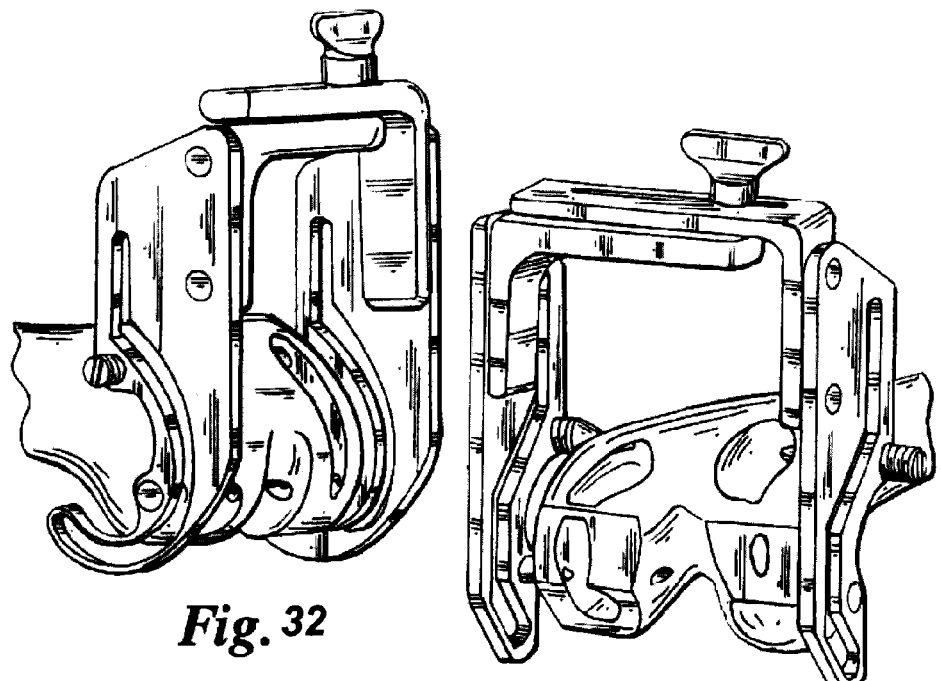

FIG. 10 also represents an embodiment of the present invention which allows for the accurate and precise preparation of curvilinear cut surfaces, beneficially used in conjunction with guides containing curvilinear guide surfaces as represented in FIGS. 31 and 32, to create cut surfaces for intimate attachment and fixation to prosthetic implants. One feature of such a device is the adjustability of the mediolateral location of the cutting profile of the cutting tool with respect to the femur prior to and/or during resection. As the ML location of the cutting tool with respect to the bone during resection dictates the ML location of the prosthesis with respect to the bone, this feature is important to whether the entirety of the cuts are made in a single sweep, or whether cuts with a linear cutting profile are performed first, and secondary cuts with curved or non-colinear cutting profiles are performed in a second step as may be desired for first cutting the femoral condyles (with a curved cutting path, but a linear cutting profile) and second cutting a trochlear or patellofemoral fixation surface with a curved cutting profile and a curved cutting path that smoothly blends into the condylar cuts. This particular embodiment of the present invention facilitates both bone preservation and femoral prosthesis designs with smooth geometric transitions between the different compartments of the joint for both its fixation surfaces and articular surfaces.

FIGS. 11 through 32

FIGS. 11 through 32 show embodiments of the present invention for Transcutaneous Transarticular Resection in TKA, DuoCondylar, Patellofemoral, and/or Unicondylar Knee Replacement. Several features are critical in effectively implementing this technique in a manner, which simultaneously promotes rapid wound healing, cosmesis via reduced incision size, and reproducibility in a manner independent of individual surgeon craftsmanship while preserving the safety and ease of use characteristics of Profile Based Resection.

Figure 5:
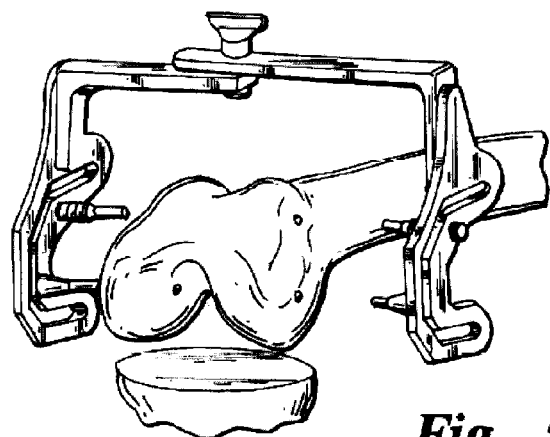
Figure 6:
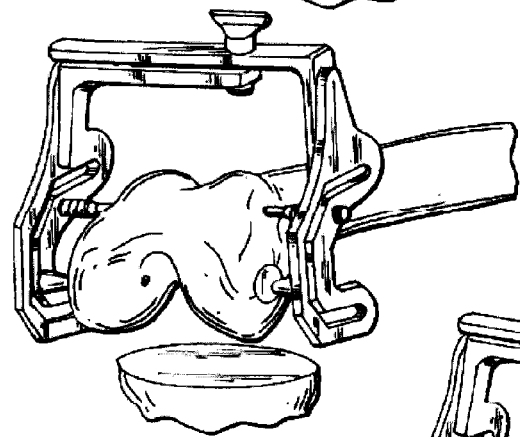
Figure 7:
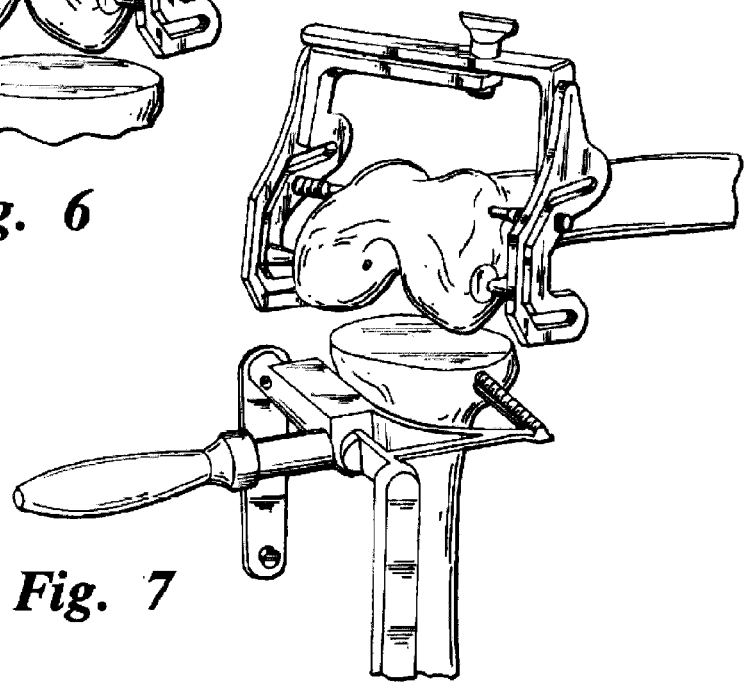
Figure 8:
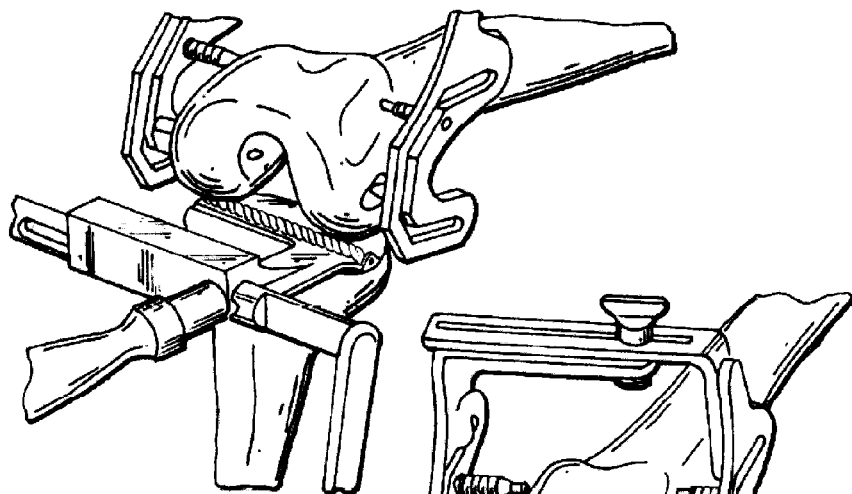
Figure 9:
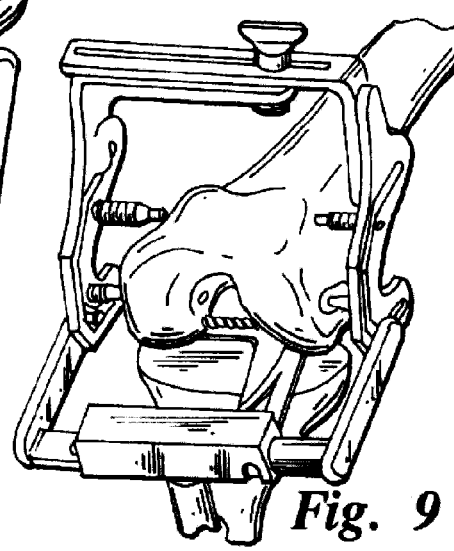
Figure 12:
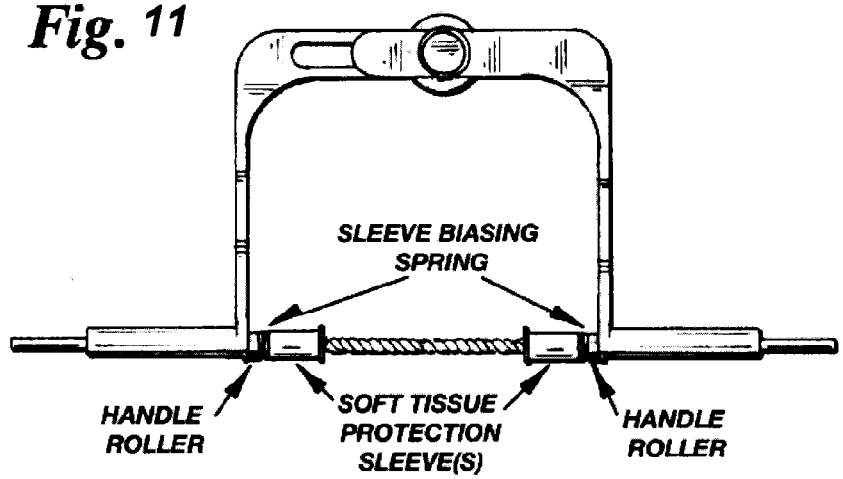
Figure 13:
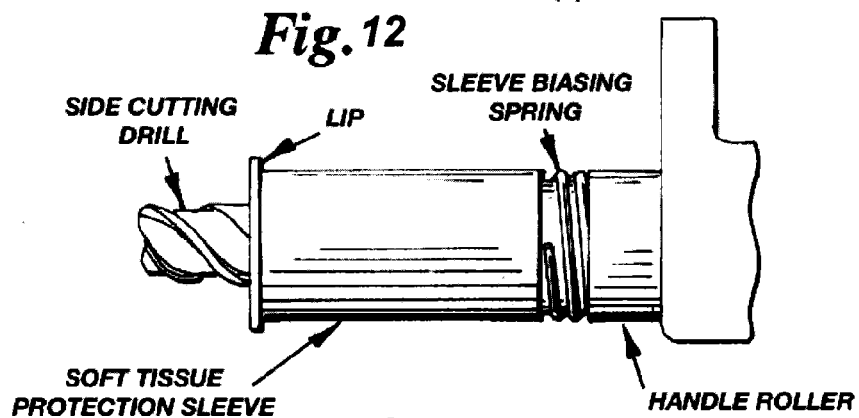
Figure 18:
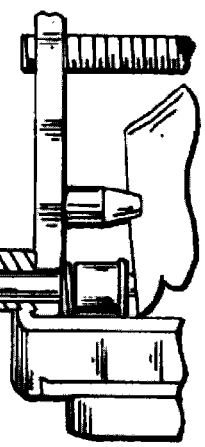
Figure 19:
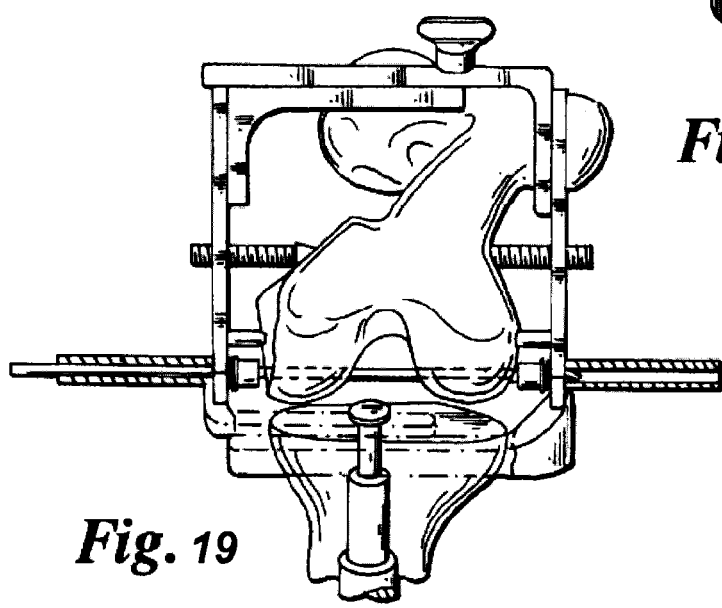
Figure 20:
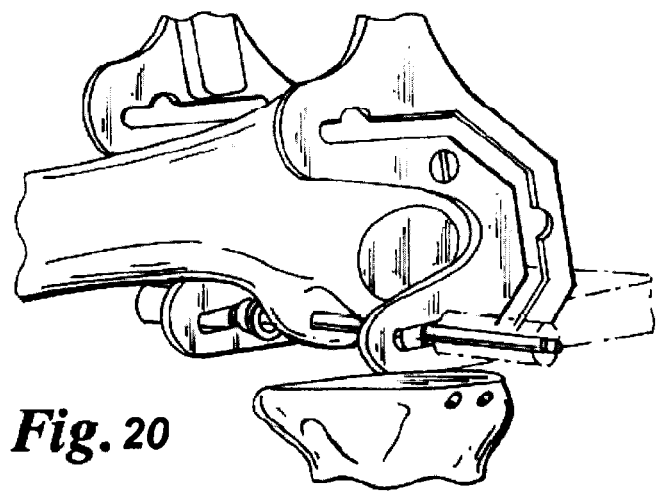
Figure 22:
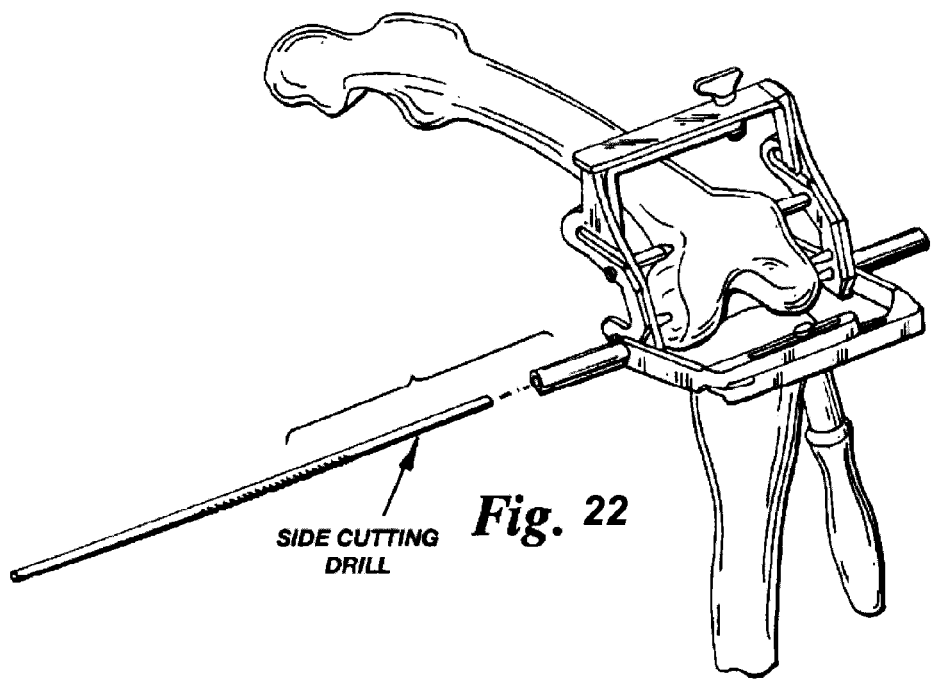
Figure 23:
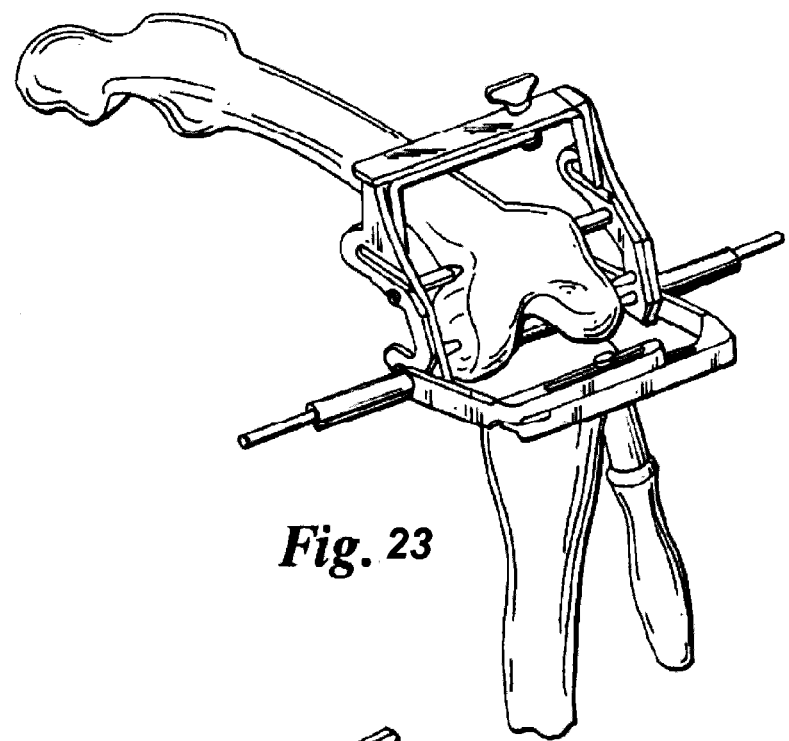
Figure 24:
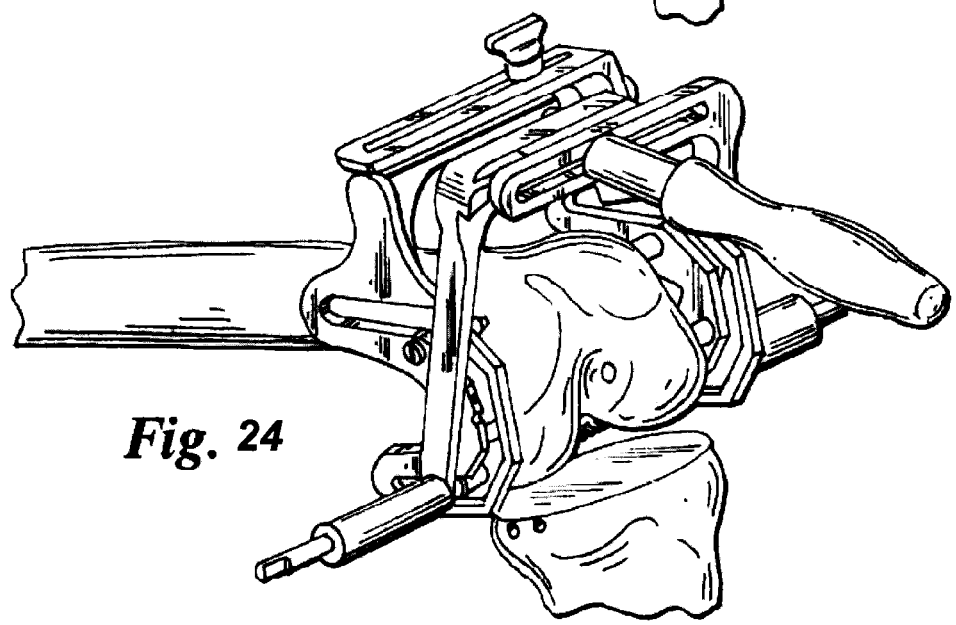
Figure 25:
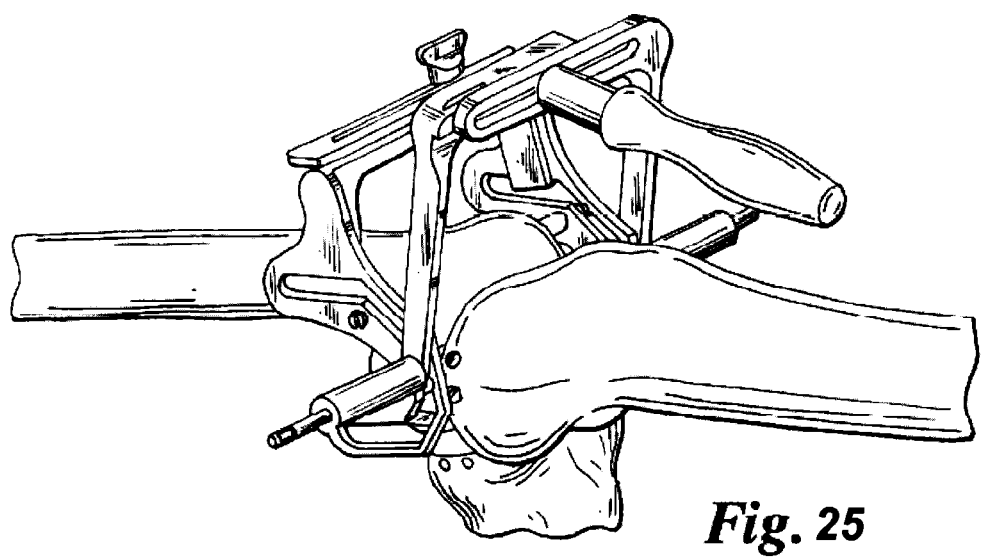
Figure 26:
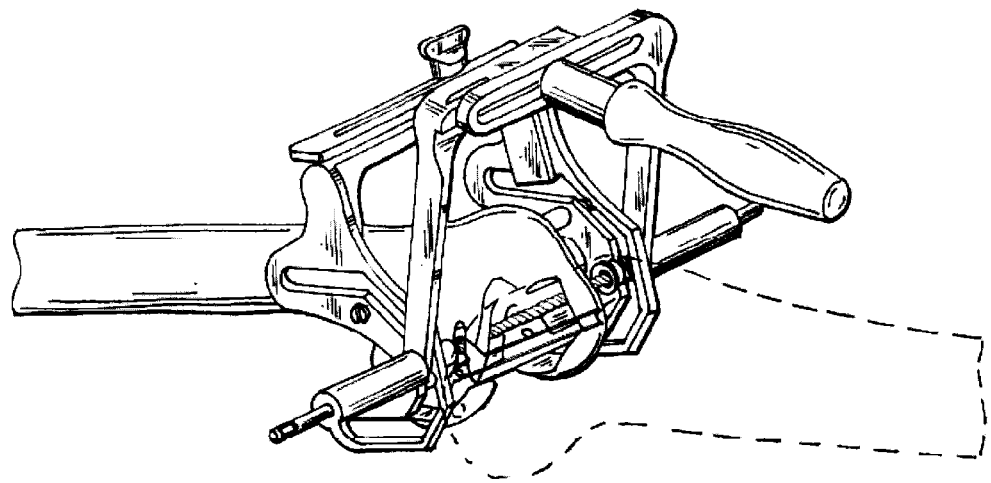
Figure 27:
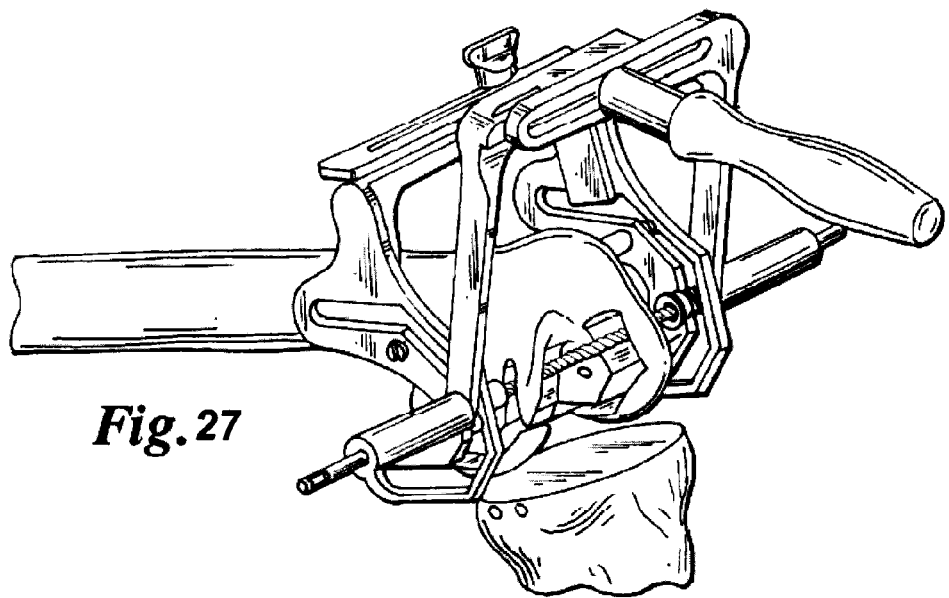
Figure 28:
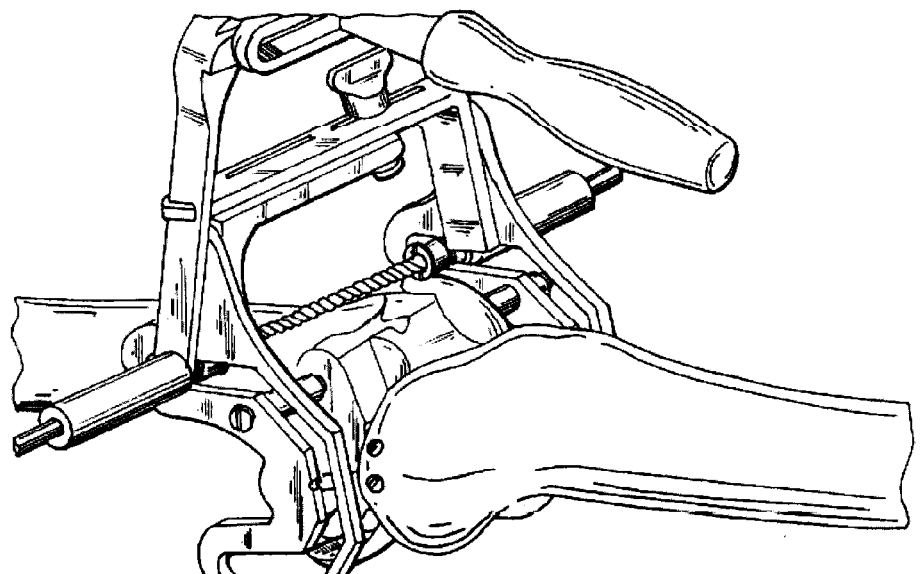
Figure 29:
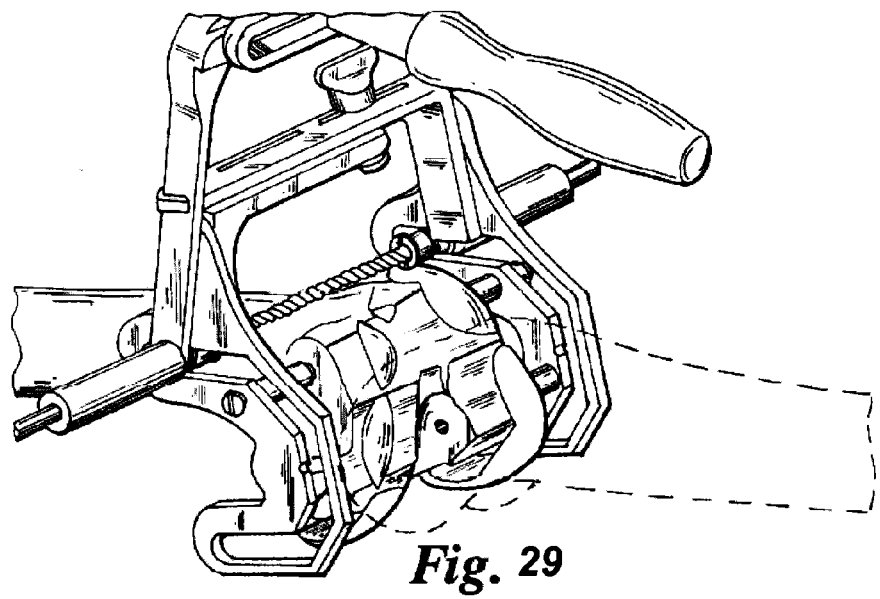
Figure 30:
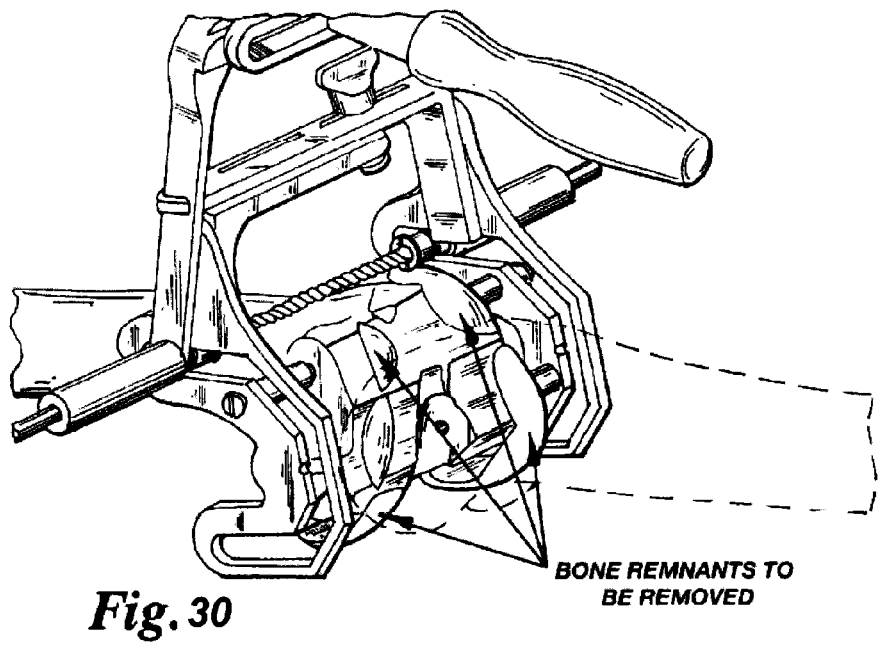

FIGS. 12 and 13 represent soft tissue protection sleeves for use in preventing or mitigating contact between soft tissues and the cutting surfaces of a cutting tool. This is particularly useful in Transcutaneous Transarticular TKA ("TTTKA" or "Triple TKA" or "T Cubed" or "T$^3$" Procedures) where a PBR cutting guide, as generally shown in FIG. 5 is positioned completely outside of the wound with the exception of fixation features which extend from the externally located guides through skin incisions and into holes or apertures created in bone. As shown in FIGS. 22 and 23, the cutting tool, in the case of the present invention a side cutting drill, is extended through the handle, the guide, the skin, fat, capsule, etc (soft tissue), across, across and in front of, through, or beneath the articular surfaces of the joint, and through the soft tissue, guide, and handle on the opposing side of the bone. The soft tissue protection sleeves may be extended through the soft tissue and into contact with the sides of the bone. The retaining lip can be used to maintain the sleeves in contact with the bone and are held there by the edges of the incision through the capsule during cutting. The springs shown in FIG. 13 can further bias the sleeves into contact with bone in a manner that would maintain that contact as the width of the bone changed along the cutting path of the resected surface.

One skilled in the art will note that the thicknesses for the soft tissue through which the sleeves extend change significantly from patient to patient thus requiring the proportions of the sleeve, spring and other components of the present embodiment of the invention to change accordingly. For example, in an obese patient, the fat layer through which the cutting tool extends can be 5 inches thick per side or more. The diameter of the soft tissue protection sleeve can be significantly reduced with respect to what is shown as the side cutting drill diameter is reduced, thus requiring a smaller capsular or other soft tissue incision or 'stab wound'.

In operation, the handle is manipulated to traverse the cutting path of the cutting guide while the tibia is swung through a range of motion about the femur as shown in comparing FIGS. 24 through 30. This particular principal of operation takes advantage of the fact that the capsule, the patella, and to a lesser or greater extent the skin, moves with the tibia as it moves through a range of motion with respect to the femur. Thus, a small, perhaps 4 mm to 10 mm long stab wound through skin to the medial side of the posterior femoral condyles (roughly in line with the axis of the pilot drill shown in FIG. 21) with the knee bent in flexion, and then looked at the side of the femur (through the portal created by the stab wound) while moving the tibia through a range of motion, the side of the femur would be observed to be passing by through the portal. In order to complete all of the resected surfaces on the femur necessary to fix a standard femoral prosthesis, it may be necessary in one embodiment to make two passes with the side cutting drill sweeping about the femur with the tibia as represented in FIGS. 24 through 30.

Figure 38:
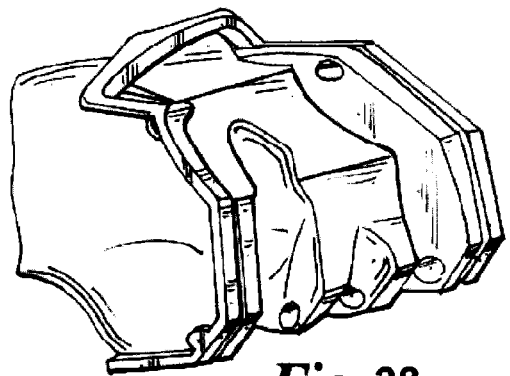

FIGS. 14 through 21 represent an embodiment of the present invention for use in creating pilot holes allowing for introduction of a side cutting drill or other cutting tool in Triple TKA or Unicondylar or Bicondylar procedures. Of particular interest, the pilot drill is designed to eliminate or mitigate any deviations of the drill from its intended location and orientation as it is guided to create portals in living bone. Standard drills tend to follow the path of least resistance into and through bone often resulting in either poor drill placement, and thereby poor cutting guide placement, or improperly located and oriented portals or apertures for fixation of a cutting guide resulting in poor cutting guide placement. As shown in FIG. 14, the pilot drill possesses cutting teeth that are very aggressive in side cutting. This is critical in that it prevents deflection of the cutting tool when it contacts tissue of varying material properties while plunging into bone in a direction co-axial with its central longitudinal axis. This area of very aggressive side cutting teeth is relatively short, and is followed by a longer smooth portion of the shaft of the drill which is designed to be incapable of cutting bone, but may beneficially include smooth flutes allowing for removal of chips during the cutting process. A pilot drill of this kind is desirable for use in creating the apertures in bone desired for positioning the cutting guides. Specifically, the pilot drill may provide sufficient accuracy and precision of aperture creation to allow for drilling all the way through or across a bone to which a cutting guide will be attached to bone sides of the aperture as shown in FIG. 38, where the cancellous bone within the cortical shell is not shown for the sake of clarity. Another important application for this embodiment of the present invention is the creation of apertures in bone to which PinPlasty type guides will be attached as the accuracy and precision of aperture creation dramatically impacts the accuracy and precision of the resulting bone cuts.

Figure 21:
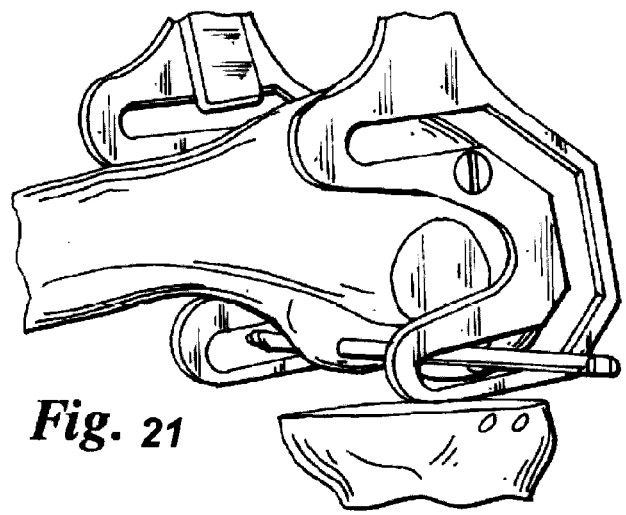

In use with the embodiment of the present invention, with the soft tissue protection sleeves of the milling handle in contact with a bone surface, the pilot drill would be plunged through the bushings of the milling handle and across the joint, as shown in FIGS. 15 through 21. FIG. 21 represents the pilot drill having been plunged entirely across the joint, but with the milling handle not shown for the sake of clarity. Thus, a portal has been created across the entirety of the joint for subsequent insertion of the side cutting drill shown in FIGS. 22 and 23, or any other cutting tool. It should be noted that in embodiments adapted for use in Unicondylar knee replacement, it would only be necessary to create the portal in one side of the joint for extension of the cutting tool across only a single condyle. An alternative embodiment and method of the milling handle of the present invention represented in FIG. 24 would be to extend the side cutting drill, or other cutting tool, through a soft tissue portal on one side of the joint, across the entirety of the bone surfaces to be resected or cut, but not extend the tool through the soft tissue on the far side of the joint. As control of the side cutting drill by the milling handle is very robust, even when it supports only one spindle of the side cutting drill, accurate and precise preparation of the distal femur can be performed without necessitating a second soft tissue portal, and the soft tissue trauma associated with it, no matter how minor, on the far side of the joint.

Alternatively, a hybrid embodiment of externally and internally located guide surfaces would allow for high precision, high accuracy cutting without necessitating the creation of soft tissue portals for insertion of the cutting tool. This embodiment of the present invention may be attained by positioning one ultra low profile PBR cutting guide surface(s) in the wound (perhaps looking like the medial guide surface of the cutting guide shown in FIGS. 38 through 40) and interconnecting it with an externally located PBR cutting guide surface(s) (perhaps looking like the laterally located plate in FIG. 30). This would allow for single spindle guidance of the side cutting drill or other cutting tool in a very robust manner, while minimizing the trauma to soft tissues necessary to implement these embodiments. Furthermore, the use of these single spindle embodiments lend themselves to easy manipulation of the cutting tool in pivotally sweeping a cut surface while manipulating the cutting tool axially with respect to the milling handle. Thus the anterior chamfer cut, distal cut, and posterior cut could be completed by sweeping the cutting tool along the cutting path of the cut surface, and the anterior and/or posterior cuts could be completed by pivotally sweeping the cutting tool as mentioned above while maintaining the stability inherent in guiding the milling handle on guide surfaces on opposing sides of the cut being created. This is beneficial in that the internally located guide surfaces could be truncated or shortened significantly allowing for both easier insertion into the surgical exposure and reduction in the exposure necessary to accommodate the embodiments in clinical use.

Figure 42:
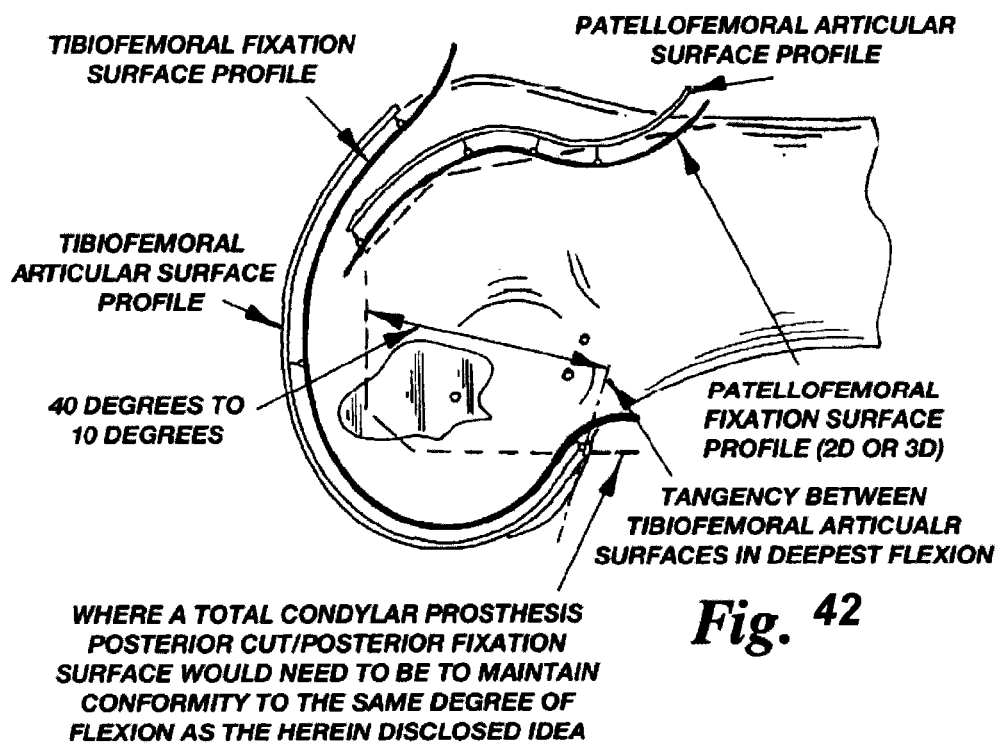
Figure 45:
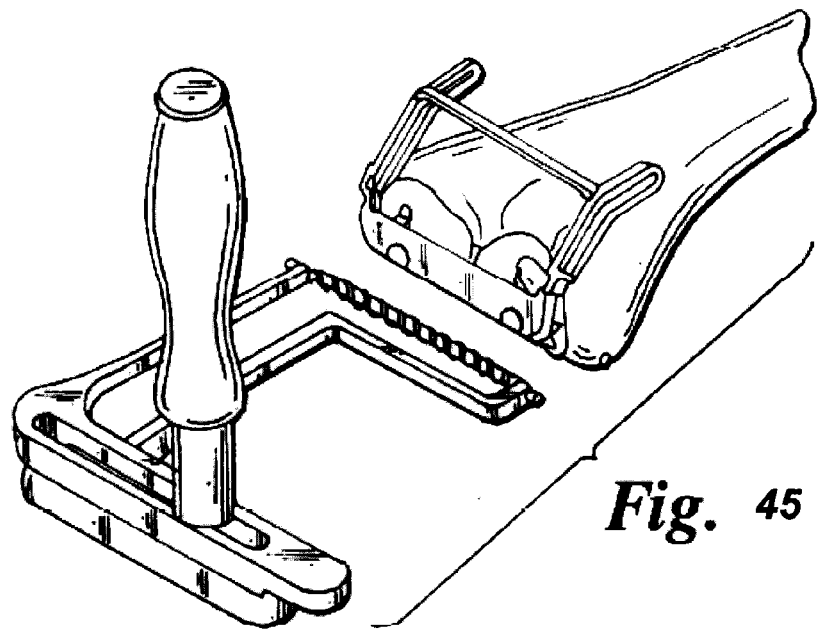

FIGS. 31 through 32, represent embodiments of the present invention for use in bone preserving resection techniques. As noted in FIGS. 31, and 42-44, a significant amount of viable bone tissue may be preserved while maintaining all functional paradigms of conventional TKA while improving articular conformity in the deepest ranges of flexion. It is of particular interest to note that this is especially applicable in improving the results of conventional Unicondylar implant performance, as the current state of the art makes minimal planar posterior cuts which prohibit articular conformity in deep flexion. This is something of a 'catch 22' as Unicondylar replacement is most often implemented in younger patients whom place higher functional demands, specifically they bend their knees more deeply than their older counterparts, on their implants, yet in an effort to preserve bone for revision, most unicondylar replacements don't possess nearly the range of motion with conformity necessary. Thus a Unicondylar design incorporating deep flexion articular surfaces (as shown in FIG. 42) and corresponding fixation surfaces could simultaneously offer articular conformity and bone preservation for these younger or more physically active patients who are more likely to demand higher performance and require revision to TKA.

Figure 34:
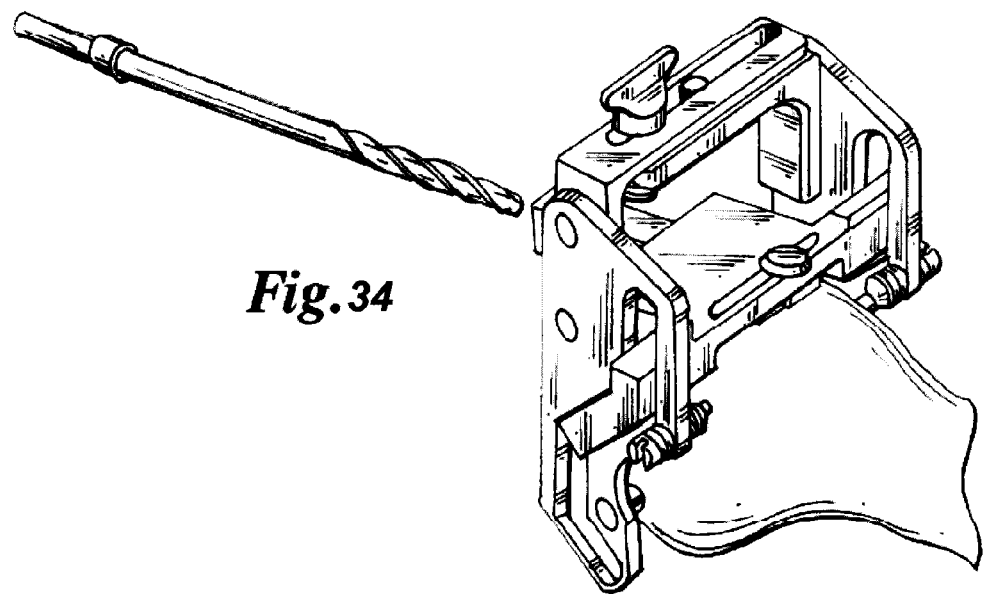
Figure 35:
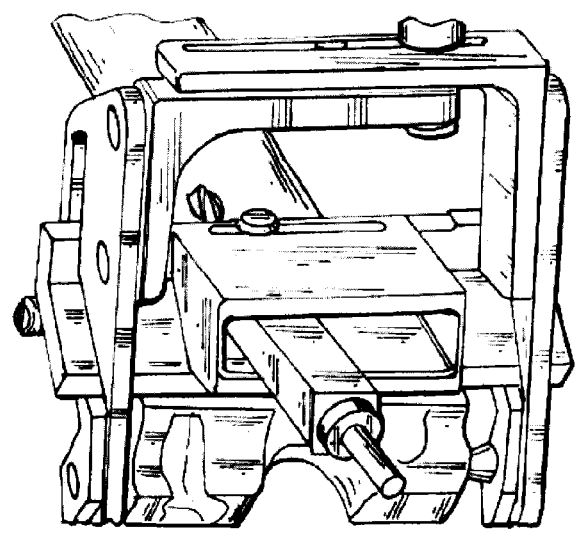
Figure 36:
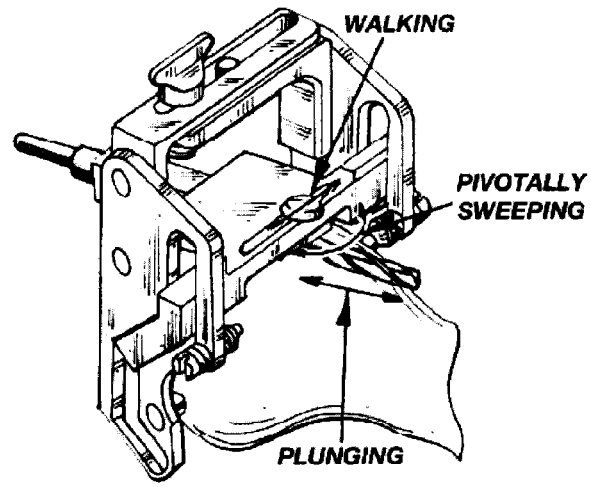
Figure 37:
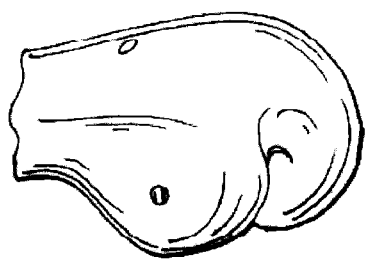

FIGS. 33 through 36 represent an embodiment of the present invention which would facilitate PBR cutting of, in one embodiment, the posterior chamfer cut, distal cut, and anterior chamfer cut, and any combination of plunging, pivotally sweeping, and walking manipulations represented in FIGS. 34 through 36 to complete the remaining cuts.

Figure 39:
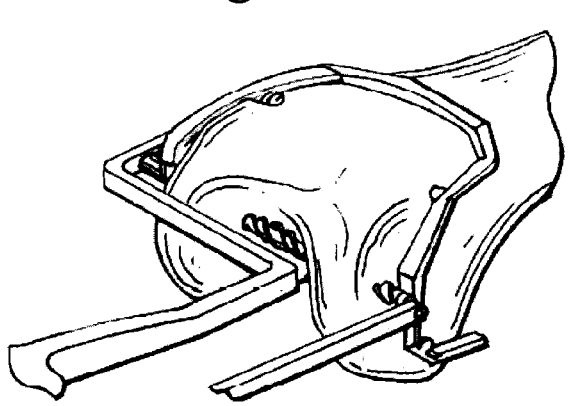
Figure 40:
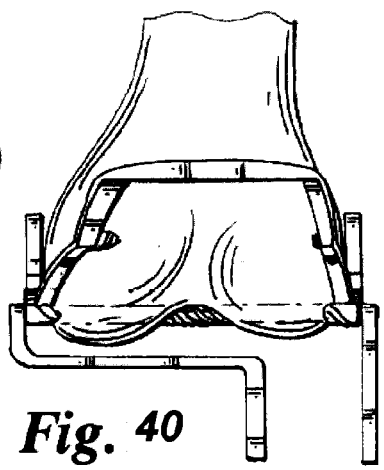
Figure 41:
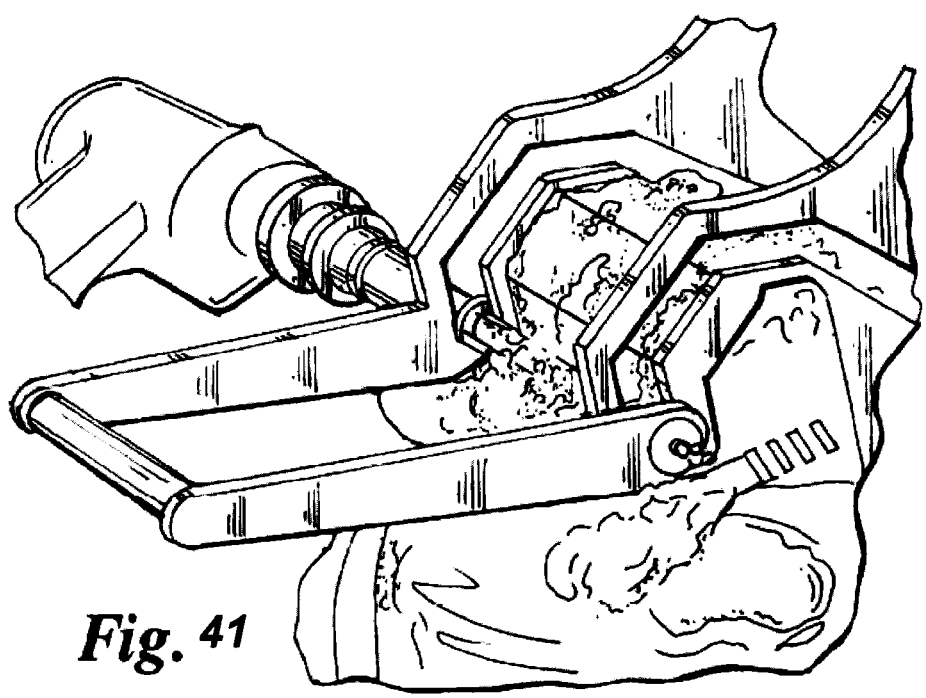

FIGS. 37 through 41 represent ultralow profile PBR embodiments of the present invention, which, as may be seen in comparing FIGS. 39 and 41, lend themselves to minimally invasive implementation while preserving the outstanding clinical performance characteristics of PBR. The embodiment of the milling handle shown utilizes milling handle retaining features of the copending provisional applications reference herein. As is seen in comparing FIGS. 37 and 38, the cutting guides shown are fixed to bone surfaces located to the sides of bone surfaces to be cut for fixation to the implant. Some surgeons may not be overly fond of creating such apertures in living tissue that while then have to heal postoperatively. This may be avoided easily by modification of the guide represented in FIG. 38. Instead of creating the apertures in bone to the sides of the cuts, the apertures are formed in bone that will be removed upon completion of the anterior chamfer cut and the posterior chamfer cut. The cutting profile of the cutting guide shown in FIG. 38 would thereby be modified to allow the cutting profile of the cutting tool to traverse a cutting path that, in one embodiment, would complete the anterior cut, a portion of the anterior chamfer cut, the distal cut, and the posterior cut. Completion of any remaining cuts could then be completed in any manner known in the art, such as using the partially cut surfaces as a guide for their completion, attachment of a cutting guide to cut surfaces (such as a conventional chamfer cutting block), or a profiled chisel with cutting surfaces or edge which possessed the exact profile, or resected surface "cutting path", of the cuts to be created and would be plunged across the surfaces being cut in a side to side or mediolateral direction. It should be noted that the profiled chisel embodiment of the present invention would be particularly useful when used in conjunction with the side to side oriented or extended embodiments of Pinplasty style cutting systems, or alternatively, for use with single plate versions of the PBR guides represented herein and/or in the copending applications referenced herein.

Preferably, an offset power input for a milling handle embodiment of the present invention. It should be noted that the mechanism represented by the yellow lines/arcs could be a chain, belt, spur gear, or other rotary power transmission linkage. This allows for a milling handle design that allows for the distal ends of the arms to be deeply inserted into a wound without the drive input displacing soft tissue (as somewhat shown in FIG. 41).

FIGS. 45 through 51

Figure 46:
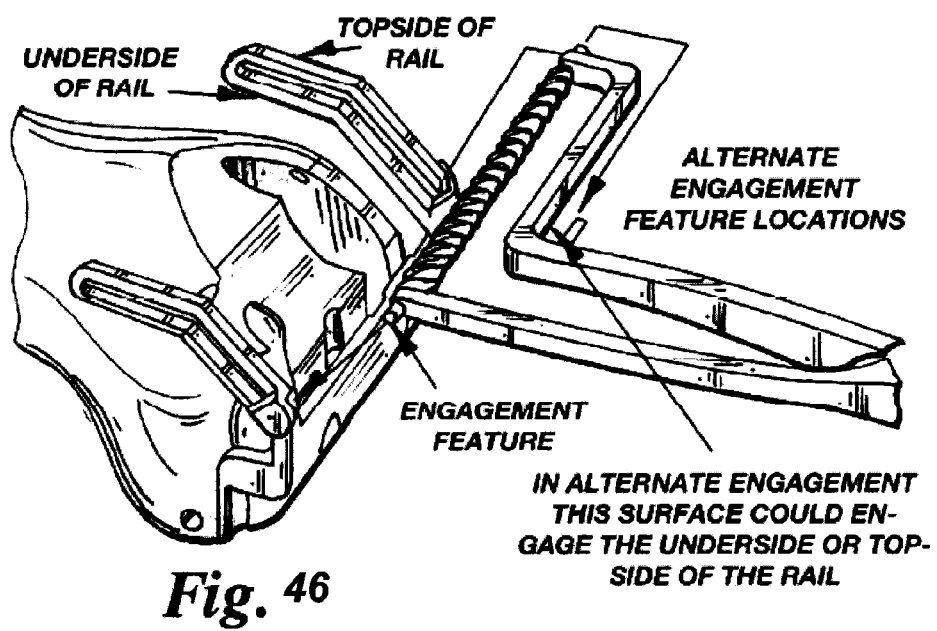
Figure 47:
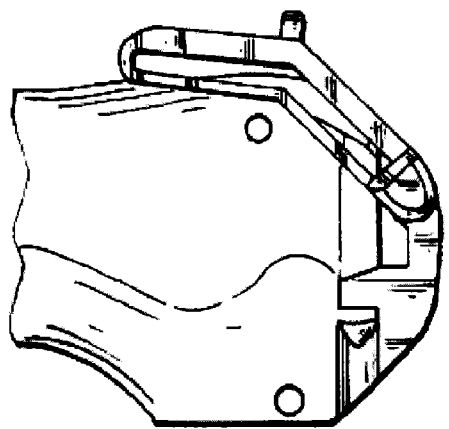
Figure 48:
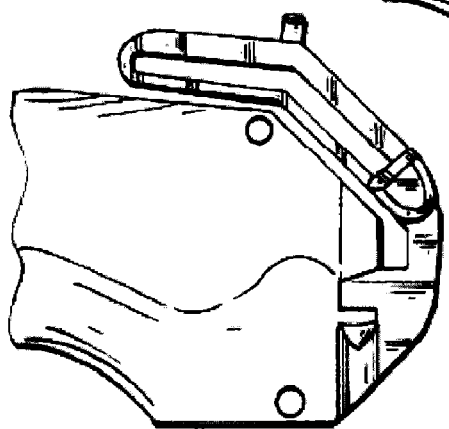
Figure 49:
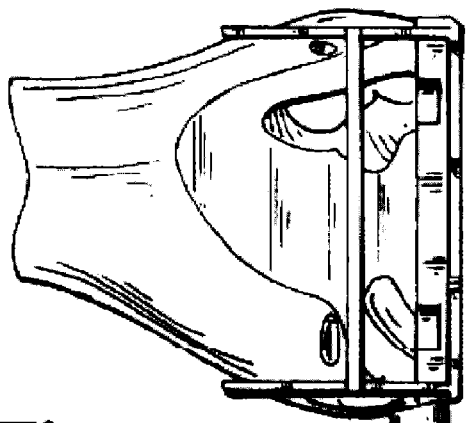
Figure 50:
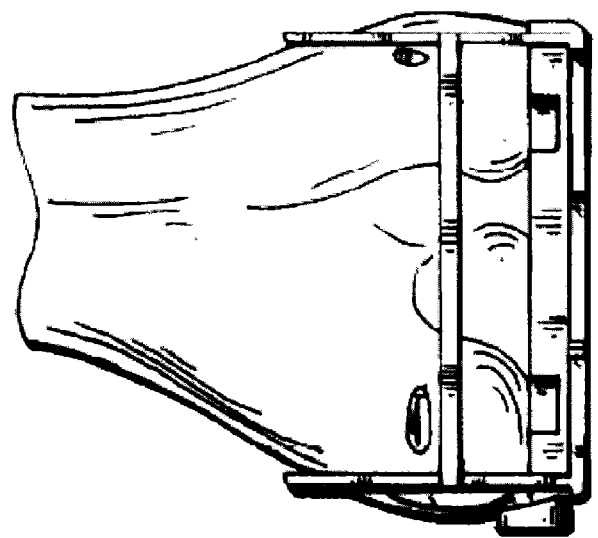
Figure 51:
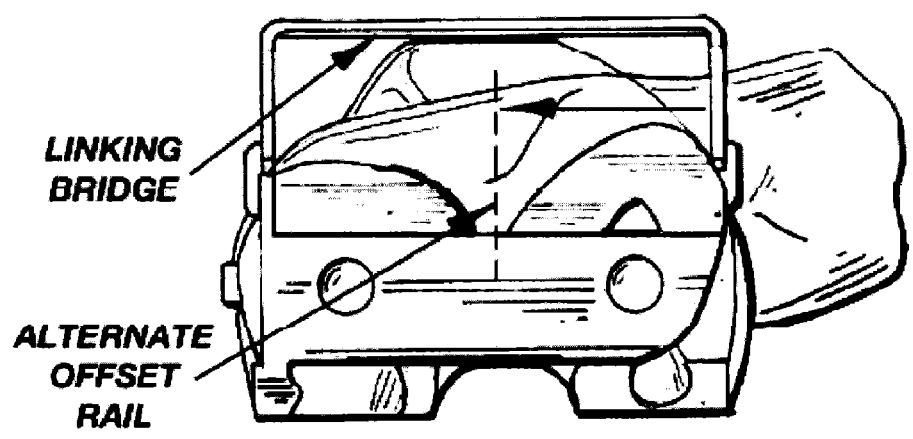

FIGS. 45 through 51 shown a PBR guide which is attached to bone surfaces located within and/or over the border of the cuts to which an implant will be fixed. FIG. 51 perhaps best shows the apertures in the distal face of the guide through which cam pins or other fixation means may extend (the fixation means could also be more standard integrally formed pins or screws). The PBR rails shown optionally possess a linking bridge shown in FIG. 51 to provide additional stability to the rails, as needed. As shown in FIG. 46, the milling handle in this embodiment possesses outwardly facing engagement features for engaging the guide surfaces of the rails and or the interior walls of the rails during cutting. FIGS. 51 and 46 further show the option of engaging alternative engagement features of the milling handle with alternative guide rails. It should be noted that although the embodiment represented in these figures is adapted for use in making cuts for standard total condylar implant fixation, such a guide and milling handle could easily be adapted to perform high precision, high accuracy trochlear groove and intercondylar cuts to accommodate the implant embodiments of the present invention. Furthermore, although the rails in FIG. 51 are shown as being flat, and located to the sides of the surfaces to be cut, it would be desirable, especially in cutting bone for cortical prosthesis attachment, the position the rails over the trochlear groove the be cut and curving or angling, as necessary, the plates out of plane. One embodiment of the present invention would then appear to be curved as observed in a mediolateral direction, and/or curved as viewed in an anterior to posterior direction, and/or curved as viewed in a distal to proximal direction to best approximate the geometry of the natural bone.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed is:

1. A method for implanting an orthopedic prosthesis during a knee arthroplasty surgery comprising:

providing a cutting tool having a cutting profile defined along a longitudinal axis and presenting an effective width of the cutting profile transverse to the longitudinal axis, the cutting tool further having a single offset handle arm extending along an arm axis generally transverse to the longitudinal axis and presenting an effective width transverse to the arm axis, such that both the effective width of the cutting profile and the effective width of the handle arm are less than an effective length of the cutting profile along the longitudinal axis;

creating an opening in tissue proximate a bone on which a resected surface is to be created during the knee arthroplasty surgery, the opening having a maximum dimension generally equal to or greater than the effective width of the handle arm and the effective width of the cutting profile and less than the effective length of the cutting profile;

utilizing the handle arm to manipulate the cutting tool into the opening such that the cutting profile is positioned to create the resected surface;

creating at least a portion of the resected surface by relative movement of the cutting tool and the bone;

utilizing the handle arm to removing the cutting tool from the opening; and operably attaching a corresponding surface of the orthopedic prosthesis to the resected surface.

2. The method of claim 1, wherein the handle arm and the cutting profile define a cutting tool with a generally L-shaped outline and wherein the step of utilizing the handle arm to manipulate the cutting tool comprises snaking first the effective length of the cutting profile and then a portion of the handle arm along the handle axis into the opening.

3. The method of claim 1, where the handle arm further comprises at least one outrigger arm proximal to the cutting profile and external to the opening when the cutting tool is positioned with the cutting profile in place to create the resected surface, the at least one outrigger arm adapted to interface with at least one external guide surface, and wherein the step of creating the at least a portion of the resected surface comprises operably engaging the at least one outrigger arm with the at least one external guide surface and moving the handle arm in a manner so the cutting tool is effectively guided by the at least one external guide surface.

4. A cutting tool to create a resected surface in a bone during a knee arthroplasty procedure, the cutting tool comprising:

a cutting profile defined along a longitudinal axis and presenting an effective width of the cutting profile transverse to the longitudinal axis; and a single offset handle arm operably connected to the cutting profile and extending along an arm axis generally transverse to the longitudinal axis and presenting an effective width transverse to the arm axis, wherein both the effective width of the cutting profile and the effective width of the handle arm are less than an effective length of the cutting profile along the longitudinal axis such that the cutting tool can be manipulated into an opening in tissue proximate the bone on which the resected surface is to be created during the knee arthroplasty procedure, the opening having a maximum dimension generally equal to or greater than the effective width of the handle arm and the effective width of the cutting profile and less than the effective length of the cutting profile.

5. The apparatus of claim 4, wherein cutting profile of the cutting tool is selected from the set consisting of: a milling tool, a wireplasty cutting tool, a band saw or a reciprocating cutting tool.

6. The apparatus of claim 4, wherein the handle arm further comprises at least one outrigger arm proximal to the cutting profile and external to the opening when the cutting tool is positioned with the cutting profile in place to create the resected surface, the at least one outrigger arm being adapted to interface with at least one external guide surface.

7. The apparatus of claim 6, wherein the handle arm includes a pair of outrigger arms and a pair of external guide surfaces mounted on opposing side of the bone to be resected.

8. The apparatus of claim 7, wherein the pair of outrigger arms are operably connected by a bridge member having a selectively adjustable width and a handle grip extending proximal from the bridge member, the bridge member being operably connected to the single offset handle arm.

9. The apparatus of claim 4, wherein the single offset handle arm further comprises means for providing a motive power to the cutting profile of the cutting tool.

10. A method comprising:

providing a cutting tool having a cutting profile defined along a longitudinal axis and presenting an effective width of the cutting profile transverse to the longitudinal axis, the cutting tool further having a single offset handle arm extending along an arm axis generally transverse to the longitudinal axis and presenting an effective width transverse to the arm axis, such that both the effective width of the cutting profile and the effective width of the handle arm are less than an effective length of the cutting profile along the longitudinal axis; and providing instructions for implanting an orthopedic prosthesis during a knee arthroplasty surgery, the instructions comprising:

creating an opening in tissue proximate a bone on which a resected surface is to be created during the knee arthroplasty surgery, the opening having a maximum dimension generally equal to or greater than the effective width of the handle arm and the effective width of the cutting profile and less than the effective length of the cutting profile;

utilizing the handle arm to manipulate the cutting tool into the opening such that the cutting profile is positioned to create the resected surface;

creating at least a portion of the resected surface by relative movement of the cutting tool and the bone;

utilizing the handle arm to removing the cutting tool from the opening; and operably attaching a corresponding surface of the orthopedic prosthesis to the resected surface.

* * * * *